US009556236B1

(12) United States Patent
Mohapatra et al.

(10) Patent No.: US 9,556,236 B1
(45) Date of Patent: Jan. 31, 2017

(54) COMPOSITIONS AND METHODS FOR TREATING RESPIRATORY SYNCYTIAL VIRUS INFECTION

(71) Applicants: Shyam S. Mohapatra, Lutz, FL (US); Nancy Lucrecia Goicochea, Tampa, FL (US); Suraj Dixit, Tampa, FL (US); Julio Garay, Tampa, FL (US)

(72) Inventors: Shyam S. Mohapatra, Lutz, FL (US); Nancy Lucrecia Goicochea, Tampa, FL (US); Suraj Dixit, Tampa, FL (US); Julio Garay, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 114 days.

(21) Appl. No.: 14/093,107

(22) Filed: Nov. 29, 2013

Related U.S. Application Data

(60) Provisional application No. 61/731,040, filed on Nov. 29, 2012.

(51) Int. Cl.

| | |
|---|---|
| ***C07K 14/005*** | (2006.01) |
| ***A61K 38/04*** | (2006.01) |
| ***A61K 38/16*** | (2006.01) |
| ***A61K 9/16*** | (2006.01) |

(52) U.S. Cl.
CPC ............... *C07K 14/005* (2013.01); *A61K 9/16* (2013.01); *A61K 38/162* (2013.01); *C12N 2760/18033* (2013.01)

(58) Field of Classification Search
None
See application file for complete search history.

(56) References Cited

U.S. PATENT DOCUMENTS

| | | | |
|---|---|---|---|
| 2007/0185096 | A1 | 8/2007 | Powell et al. |
| 2012/0142890 | A1 | 6/2012 | Mariani et al. |

OTHER PUBLICATIONS

Lardelli and Lendahl, Experimental Cell Research, 1993, 204:364-372.*

Ortwin Adams, et al.; Palivizumab-Resistant Human Respiratory Syncytial Virus Infection in Infancy; Brief Report, Clinical Infection Diseases (Jul. 2010); 185-188; 4 pages.

Wei-Dong Ding, et al.; Novel and Specific Respiratory Syncytial Virus Inhibitors That Target Virus Fusion; J. Med. Chem (1998); 2671-2675; 5 pages.

Suraj K. Dixit, et al.; Quantum Dot Encapsulation in Viral Capsids; NANO Letters, vol. 6, No. 9 (2006); 1993-1999; 7 pages.

Benoit Dubertret, et al.; In Vivo Imaging of Quantum Dots Encapsulated in Phospholipid Micelles; Science, vol. 298, (2002); 1759-1762; 5 pages.

Hermann J. Gruber, et al.; Preparation of Thiol-Reactive Cy5 Derivatives from Commercial Cy5 Succinimidyl Ester; Bioconjugate Chem, vol. 11 (2000); 161-166; 6 pages.

Caroline Breese Hall, M.D.; Respiratory Syncytial Virus and Parainfluenza Virus; Medical Progress; N Engl J Med, vol. 344, No. 25 (Jun. 2001); 1917-1928; 12 pages.

Zhenhua Ling, et al.; Purification and Characterization of Recombinant Human Respiratory Syncytial Virus Nonstructural Protein NSI; ScienceDirect, Protein Expression and Purification 57 (2008); 261-270; 10 pages.

Peter J. M. Openshaw, PHD, FRCP, et al.; Links Between Respiratory Syncytial Virus Bronchiolitis and Childhood Asthma: Clinical and Research Approaches; Pediatr Infect Dis J, vol. 22, No. 2 (2003); S58-S65; 8 pages.

Amanda Trent, et al.; Structural Properties of Soluble Peptide Amphiphile Micelles; Soft Matter, 7 (2011); 9572-9582; 11 pages.

Enxiu Wang, et al.; Both Heptad Repeats of Human Respiratory Syncytial virus Fusion Protein are Potent Inhibitors of Viral Fusion; Science Direct, Biochemical and Biophysical Research Communication 302 (2003); 469-475; 7 pages.

Kenneth L. Powell, et al.; Development of Antivirals Against Respiratory Syncytial Virus; Respiratory Syncytial Virus, DOI 10,1016/S0168-7069(06)14009-4 (2007); 279-297; 19 pages.

Kuo-Long Yu, et al, Respiratory Syncytial virus fusion inhibitors. Part 4: Optimization for oral bioavailability, www.ScienceDirect.com, 2006 Elsevier Ltd, 7 pages.

Marie-Claude Rouan, et al, Pharmacokinetics-Pharmacodynamics of a Respiratory Syncytial Virus Fusion Inhibitor in the Cotton Rat Model, Antimicrobial Agents and Chemotherapy, Nov. 2010, 6 pages.

Minyoung Park, et al, A fluorescence polarization assay using an engineered human respiratory syncytial virus F protein as a direct screening platform, Analytical Biochemistry—www.elsevier.com, 2010, 7 pages.

Dirk Roymans, et al., Binding of a potent small-molecule inhibitor of six-helix bundle formation requires interactions with both heptad-repeats of the RSV fusion protein, PNAS, Jan. 5, 2010, 6 pages.

* cited by examiner

*Primary Examiner* — Stacy B Chen
(74) *Attorney, Agent, or Firm* — Thomas Horstemeyer, LLP

(57) ABSTRACT

Briefly described, embodiments of the present disclosure relate to isolated polypeptides useful for treatment of respiratory syncytial virus, and to methods and compositions for treating respiratory syncytial virus.

13 Claims, 12 Drawing Sheets

A

| | | |
|---|---|---|
| SEQ ID NO: 1 | HR2 | GSSDEFDASISQVNEKINQSLAFIRRSDELLHNVNTGKSTTNY |
| SEQ ID NO: 2 | HR2-S | FDACISQVNECINQSLAFIRKSDELLHNVNAGKST |
| SEQ ID NO: 3 | HR2-E | FDASISQVNEKINQSLAFICKSDELLCNVNAGKST |
| SEQ ID NO: 4 | HR2-A | FDACISQVNECINQSLAFICKSDELLCNVNAGKST |
| SEQ ID NO: 5 | HR2-B | GISQVNEGKSDELLG |
| SEQ ID NO: 6 | HR2-C | GCISQVNECKSDELLCG |
| SEQ ID NO: 7 | HR2-D | DACISQVNECINQSLAFICKSDELLCNT |

SEQUENCE LISTING

```
<160> NUMBER OF SEQ ID NOS: 14

<210> SEQ ID NO 1
<211> LENGTH: 43
<212> TYPE: PRT
<213> ORGANISM: respiratory syncytial virus

<400> SEQUENCE: 1

Gly Ser Ser Asp Glu Phe Asp Ala Ser Ile Ser Gln Val Asn Glu Lys
1               5                   10                  15

Ile Asn Gln Ser Leu Ala Phe Ile Arg Arg Ser Asp Glu Leu Leu His
            20                  25                  30

Asn Val Asn Thr Gly Lys Ser Thr Thr Asn Tyr
        35                  40
```

-continued

<210> SEQ ID NO 2
<211> LENGTH: 35
<212> TYPE: PRT
<213> ORGANISM: Artificial Sequence
<220> FEATURE:
<223> OTHER INFORMATION: Chemicaly synthesized anti-RSV peptide

<400> SEQUENCE: 2

```
Phe Asp Ala Cys Ile Ser Gln Val Asn Glu Cys Ile Asn Gln Ser Leu
1               5                   10                  15

Ala Phe Ile Arg Lys Ser Asp Glu Leu Leu His Asn Val Asn Ala Gly
            20                  25                  30

Lys Ser Thr
        35
```

<210> SEQ ID NO 3
<211> LENGTH: 35
<212> TYPE: PRT
<213> ORGANISM: Artificial Sequence
<220> FEATURE:
<223> OTHER INFORMATION: Chemically synthesized anti-RSV peptide

<400> SEQUENCE: 3

```
Phe Asp Ala Ser Ile Ser Gln Val Asn Glu Lys Ile Asn Gln Ser Leu
1               5                   10                  15

Ala Phe Ile Cys Lys Ser Asp Glu Leu Leu Cys Asn Val Asn Ala Gly
            20                  25                  30

Lys Ser Thr
        35
```

<210> SEQ ID NO 4
<211> LENGTH: 35
<212> TYPE: PRT
<213> ORGANISM: Artificial Sequence
<220> FEATURE:
<223> OTHER INFORMATION: Chemically synthesized anti-RSV peptide

<400> SEQUENCE: 4

```
Phe Asp Ala Cys Ile Ser Gln Val Asn Glu Cys Ile Asn Gln Ser Leu
1               5                   10                  15

Ala Phe Ile Cys Lys Ser Asp Glu Leu Leu Cys Asn Val Asn Ala Gly
            20                  25                  30

Lys Ser Thr
        35
```

<210> SEQ ID NO 5
<211> LENGTH: 15
<212> TYPE: PRT
<213> ORGANISM: Artificial Sequence
<220> FEATURE:
<223> OTHER INFORMATION: Chemically synthesized anti-RSV peptide

<400> SEQUENCE: 5

```
Gly Ile Ser Gln Val Asn Glu Gly Lys Ser Asp Glu Leu Leu Gly
1               5                   10                  15
```

<210> SEQ ID NO 6
<211> LENGTH: 17
<212> TYPE: PRT
<213> ORGANISM: Artificial Sequence
<220> FEATURE:
<223> OTHER INFORMATION: Chemically synthesized anti-RSV peptide -continued

<400> SEQUENCE: 6

Gly Cys Ile Ser Gln Val Asn Glu Cys Lys Ser Asp Glu Leu Leu Cys
1 5 10 15

Gly

<210> SEQ ID NO 7
<211> LENGTH: 28
<212> TYPE: PRT
<213> ORGANISM: Artificial Sequence
<220> FEATURE:
<223> OTHER INFORMATION: Chemically synthesized anti-RSV peptide

<400> SEQUENCE: 7

Asp Ala Cys Ile Ser Gln Val Asn Glu Cys Ile Asn Gln Ser Leu Ala
1 5 10 15

Phe Ile Cys Lys Ser Asp Glu Leu Leu Cys Asn Thr
20 25

<210> SEQ ID NO 8
<211> LENGTH: 28
<212> TYPE: PRT
<213> ORGANISM: Artificial Sequence
<220> FEATURE:
<223> OTHER INFORMATION: Chemically synthesized anti-RSV peptide

<400> SEQUENCE: 8

Asp Ala Ser Ile Ser Gln Val Asn Glu Lys Ile Asn Gln Ser Leu Ala
1 5 10 15

Phe Ile Arg Lys Ser Asp Glu Leu Leu His Asn Thr
20 25

<210> SEQ ID NO 9
<211> LENGTH: 28
<212> TYPE: PRT
<213> ORGANISM: Artificial Sequence
<220> FEATURE:
<223> OTHER INFORMATION: Chemically synthesized anti-RSV peptide

<400> SEQUENCE: 9

Asp Ala Cys Ile Ser Gln Val Asn Glu Lys Ile Asn Gln Ser Leu Ala
1 5 10 15

Phe Ile Cys Lys Ser Asp Glu Leu Leu Cys Asn Thr
20 25

<210> SEQ ID NO 10
<211> LENGTH: 28
<212> TYPE: PRT
<213> ORGANISM: Artificial Sequence
<220> FEATURE:
<223> OTHER INFORMATION: Chemically synthesized anti-RSV peptide

<400> SEQUENCE: 10

Asp Ala Cys Ile Ser Gln Val Asn Glu Cys Ile Asn Gln Ser Leu Ala
1 5 10 15

Phe Ile Arg Lys Ser Asp Glu Leu Leu Cys Asn Thr
20 25

<210> SEQ ID NO 11
<211> LENGTH: 28
<212> TYPE: PRT
<213> ORGANISM: Artificial Sequence
<220> FEATURE:
<223> OTHER INFORMATION: Chemically synthesized anti-RSV peptide -continued

```
<400> SEQUENCE: 11

Asp Ala Cys Ile Ser Gln Val Asn Glu Lys Ile Asn Gln Ser Leu Ala
1               5                   10                  15

Phe Ile Arg Lys Ser Asp Glu Leu Leu Cys Asn Thr
            20                  25


<210> SEQ ID NO 12
<211> LENGTH: 28
<212> TYPE: PRT
<213> ORGANISM: Artificial Sequence
<220> FEATURE:
<223> OTHER INFORMATION: Chemically synthesized anti-RSV peptide

<400> SEQUENCE: 12

Asp Ala Ser Ile Ser Gln Val Asn Glu Cys Ile Asn Gln Ser Leu Ala
1               5                   10                  15

Phe Ile Cys Lys Ser Asp Glu Leu Leu His Asn Thr
            20                  25


<210> SEQ ID NO 13
<211> LENGTH: 6
<212> TYPE: PRT
<213> ORGANISM: Artificial Sequence
<220> FEATURE:
<223> OTHER INFORMATION: Portion of a chemically synthesized anti-RSV
      peptide

<400> SEQUENCE: 13

Ile Ser Gln Val Asn Glu
1               5


<210> SEQ ID NO 14
<211> LENGTH: 5
<212> TYPE: PRT
<213> ORGANISM: Artificial Sequence
<220> FEATURE:
<223> OTHER INFORMATION: Portion of a chemically synthesized anti-RSV
      peptide

<400> SEQUENCE: 14

Ser Asp Glu Leu Leu
1               5
```

COMPOSITIONS AND METHODS FOR TREATING RESPIRATORY SYNCYTIAL VIRUS INFECTION

CROSS-REFERENCE TO RELATED APPLICATION

This application claims priority to and the benefit of U.S. provisional patent application entitled "Compositions and Methods for Treating Respiratory Syncytial Virus Infection", Ser. No. 61/731,040 filed Nov. 29, 2012 and incorporated herein by reference in its entirety.

STATEMENT AS TO RIGHTS TO INVENTIONS MADE UNDER FEDERALLY SPONSORED RESEARCH AND DEVELOPMENT

This invention was made with government support under HL101265 awarded by the National Institute of Health and CA152005 awarded by the National Cancer Institute. The Government has certain rights in this invention.

SEQUENCE LISTING

The instant application contains a sequence listing which has been submitted with the instant application. The sequence listing file is named 292103-1700_ST25.txt, is 6 KB in size, and is incorporated herein by reference in its entirety.

BACKGROUND

Respiratory syncytial virus (RSV) causes the majority of cases of bronchiolitis and acute lower respiratory tract infection in infants and young children and is also a serious threat to immunocompromised individuals and the elderly.[1-5] Hospitalization in the U.S. for RSV-associated infection in pediatric patients costs over 300 million dollars annually,[6] and no effective vaccine is currently available. Furthermore, the commercial vaccine palivizumab, only used for high-risk infants, is very expensive and its accessibility is problematic in third world countries.[9] The lack of both a vaccine and a cost-effective antiviral treatment for children, the elderly, and immunocompromised patients has created an urgent need for the development of new methodologies for RSV treatment worldwide.

Since the market approval of Palivizumab[9-11] (a prophylaxis given to high risk individuals that utilizes a monoclonal antibody that binds to the antigenic site of the RSV F protein and blocks virus entry at the initial stage of infection), several independent studies have focused on the design of inhibitors of the RSV F fusion protein.[7,8] Research is also being done to test small-molecule inhibitors[3] and RSV F inhibitor peptides[12] targeting heptad repeat (HR) domains within the fusion protein combined with biocompatible nanomaterials such as chitosan for targeted delivery.[1] Recent structural studies have demonstrated how small synthesized peptides can bind to a site on the F protein where the six-helix bundles are formed by the interaction of HR1 and HR2[13,14] and block this interaction.[3] These peptides contain a sequence of amino acids that are part of the heptad repeat sequence that specifically binds to the HR2 domain of the F protein through coiled-coiled interactions; such binding prevents fusion of the virus with the host cell membrane.[2,3] A major drawback of this antiviral strategy, however, is that the peptides are rapidly degraded by proteases in the body, thus requiring high doses to reduce infection. Moreover, the short half-life of peptides in the cells makes therapeutic use difficult. Therefore, prolonging the activity of such peptides using a delivery platform that delays the interaction of proteases with the peptides is desired.

SUMMARY

Briefly described, the present disclosure provides isolated polypeptides and methods and compositions for treating respiratory syncytial virus infection.

Embodiments of the present disclosure include, isolated polypeptides including an amino acid sequence derived from a heptad repeat (HR) domain region of an RSV F protein, where the isolated polypeptide includes at least one mutation such that the polypeptide sequence includes at least two cysteines spaced about 4 to about 7 amino acids apart, where the cysteines are capable of forming at least one disulfide linkage.

Embodiments of isolated polypeptides of the present disclosure include an isolated polypeptide including an amino acid sequence selected from the following: SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12.

The present disclosure provides embodiments of compositions including a micelle having a lipid layer and a core, where the core includes a first polypeptide, and where the first polypeptide includes an amino acid sequence selected from the following: SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12. In embodiments, the micelle also has a coating, where the coating includes a second polypeptide including an amino acid sequence selected from the following: SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12.

In embodiments, the present disclosure also provides methods of treating a respiratory syncytial virus infection in a subject. Embodiments of the methods include administering to the subject a pharmaceutically effective amount of a composition including a micelle having a lipid layer and a core, where the core includes a first polypeptide including an amino acid sequence selected from the following: SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12. In some embodiments, the micelle also includes a coating, where the coating includes a second polypeptide including an amino acid sequence selected from the following: SEQ ID NO:2, SEQ ID NO:3, SEQ ID NO:4, SEQ ID NO:5, SEQ ID NO:6, SEQ ID NO:7, SEQ ID NO:8, SEQ ID NO:9, SEQ ID NO:10, SEQ ID NO:11, and SEQ ID NO:12.

Other systems, methods, features, and advantages of the present disclosure will be or become apparent to one with skill in the art upon examination of the following drawings and detailed description. It is intended that all such additional systems, methods, features, and advantages be included within this description, and be within the scope of the present disclosure.

BRIEF DESCRIPTION OF THE DRAWINGS

The disclosure can be better understood with reference to the following drawings, which are discussed in the description and examples below. The components in the drawings are not necessarily to scale, emphasis instead being placed upon clearly illustrating the principles of the present disclosure.

DETAILED DESCRIPTION

Figure 1:
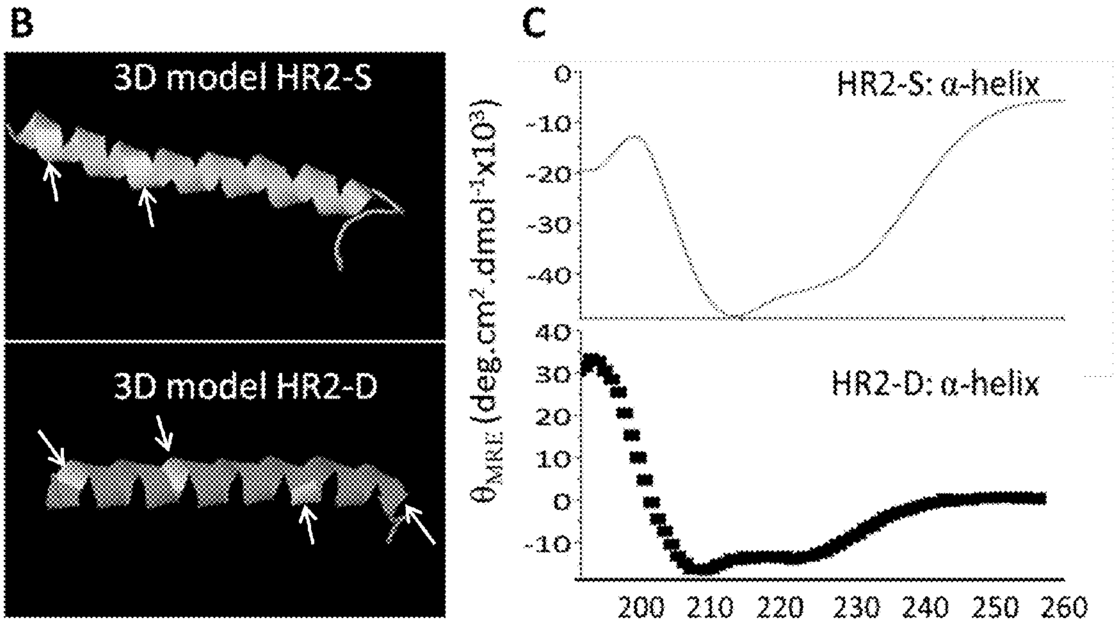
FIG. 1A illustrates the amino acid sequences of the HR2 sequence (SEQ ID NO: 1) and the synthetic peptides tested (SEQ ID NOs: 2-7); the over-line indicates disulfide linkages.
FIG. 1B illustrates a three-dimensional structure modeling of synthetic HR2-S and HR2-D peptides using structure prediction software phyre$^2$ where cysteines are indicated with white arrows.
FIG. 1C illustrates circular dichroism (CD) spectra of HR2-S and HR2-D peptides.

The details of some embodiments of the present disclosure are set forth in the description below. Other features, objects, and advantages of the present disclosure will be apparent to one of skill in the art upon examination of the following description, drawings, examples and claims. It is intended that all such additional systems, methods, features, and advantages be included within this description, be within the scope of the present disclosure, and be protected by the accompanying claims.

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of molecular biology, organic chemistry, biochemistry, bioengineering, genetics, and the like, which are within the skill of the art. Such techniques are explained fully in the literature.

It must be noted that, as used in the specification and the appended claims, the singular forms "a," "an," and "the" include plural referents unless the context clearly dictates otherwise. For example, the term "a cell" includes a plurality of cells, including mixtures thereof.

In this specification and in the claims that follow, reference will be made to a number of terms that shall be defined to have the following meanings unless a contrary intention is apparent.

DEFINITIONS

In describing and claiming the disclosed subject matter, the following terminology will be used in accordance with the definitions set forth below.

When referring to a subject or patient, the term "administering" refers to an administration that is oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, by inhalation or via an implanted reservoir. The term "parenteral" includes subcutaneous, intravenous, intramuscular, intra-articular, intraperitoneal, intra-synovial, intrasternal, intrathecal, intrahepatic, intralesional, and intracranial injections or infusion techniques. Is some embodiments, the administration is intravenous.

It should be understood that the term "coating" does not require a complete coverage of the coated object and that partial coverage is encompassed by the term. The peptide adsorption methods described herein achieve such coating.

As used herein, the term "comprising" is intended to mean that the compositions and methods include the recited elements, but not excluding others. "Consisting essentially of," when used to define compositions and methods, shall mean excluding other elements of any essential significance to the combination, and for peptides shall mean excluding amino acids that would change the function of the peptide or otherwise interfere with its intended purpose. Thus, a composition consisting essentially of the elements as defined herein would not exclude trace contaminants from the isolation and purification method and pharmaceutically acceptable carriers, such as phosphate buffered saline, preservatives, and the like. Similarly, a peptide sequence consisting essentially of a specified amino acid sequence would not exclude additional amino acids on either end of the sequence that do not interfere with the intended purpose/function of the peptide sequence. "Consisting of" shall mean excluding more than trace elements of other ingredients (for compositions), additional amino acids (for peptide sequences), and substantial method steps for administering the compositions of this disclosure. Embodiments defined by each of these transition terms are within the scope of this disclosure.

An "effective amount" is an amount sufficient to produce beneficial or desired results. An effective amount can be administered in one or more administrations, applications or dosages.

The term "isolated" means separated from constituents, cellular and otherwise, in which the polynucleotide, peptide, polypeptide, protein, antibody, or fragments thereof, are normally associated with in nature. In one aspect of this disclosure, an isolated polynucleotide is separated from the 3' and 5' contiguous nucleotides with which it is normally associated with in its native or natural environment, e.g., on the chromosome. As is apparent to those of skill in the art, a non-naturally occurring polynucleotide, peptide, polypeptide, protein, antibody, or fragments thereof, does not require "isolation" to distinguish it from its naturally occurring counterpart. In addition, a "concentrated," "separated" or "diluted" polynucleotide, peptide, polypeptide, protein, antibody, or fragments thereof, is distinguishable from its naturally occurring counterpart in that the concentration or number of molecules per volume is greater than "concentrated" or less than "separated" than that of its naturally occurring counterpart. A polynucleotide, peptide, polypeptide, protein, antibody, or fragments thereof, which differs from the naturally occurring counterpart in its primary sequence or for example, by its glycosylation pattern, need not be present in its isolated form since it is distinguishable from its naturally occurring counterpart by its primary sequence, or alternatively, by another characteristic such as glycosylation pattern. Although not explicitly stated for each of the embodiments disclosed herein, it is to be understood that all of the above embodiments for each of the compositions disclosed below and under the appropriate conditions, are provided by this disclosure. Thus, a non-naturally occurring polynucleotide is provided as a separate embodiment from the isolated naturally occurring polynucleotide. A protein produced in a bacterial cell is provided as a separate embodiment from the naturally occurring protein isolated from a eukaryotic cell in which it is produced in nature.

As used herein, the term "micelle" refers to an aggregation of molecules wherein hydrophobic portions of the molecules make up the interior of the aggregation and hydrophilic portions of the molecules make up the exterior of the aggregation.

A "pharmaceutical composition" is intended to include the combination of an active agent with a carrier, inert or active, making the composition suitable for diagnostic or therapeutic use in vitro, in vivo or ex vivo.

The term "pharmaceutically acceptable carrier or excipient" means a carrier or excipient that is useful in preparing a pharmaceutical composition that is generally safe, non-toxic and neither biologically nor otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient. As used herein, the term "pharmaceutically acceptable carrier" encompasses any of the standard pharmaceutical carriers, such as a phosphate buffered saline solution, water, and emulsions, such as an oil/water or water/oil emulsion, and various types of wetting agents. The compositions also can include stabilizers and preservatives.

The term "pharmaceutically acceptable salts" refers to any acid or base addition salt whose counter-ions are non-toxic to the subject to which they are administered in pharmaceutical doses of the salts. Specific examples of pharmaceutically acceptable salts are provided below.

The terms "pharmaceutically effective amount," "therapeutically effective amount" or "therapeutically effective dose" refers to the amount of a compound that will elicit the biological or medical response of a tissue, system, animal, or human that is being sought by the researcher, veterinarian, medical doctor or other clinician.

The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disorder or conditions and its severity, the route of administration, time of administration, rate of excretion, drug combination, judgment of the treating physician, dosage form, and the age, weight, general health, sex and/or diet of the subject to be treated.

The terms "polynucleotide" and "oligonucleotide" are used interchangeably and refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, polynucleotide probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

A polynucleotide is composed of a specific sequence of four nucleotide bases: adenine (A); cytosine (C); guanine (G); thymine (T); and uracil (U) for thymine (T) when the polynucleotide is RNA. Thus, the term "polynucleotide sequence" is the alphabetical representation of a polynucleotide molecule. This alphabetical representation can be input into databases in a computer having a central processing unit and used for bioinformatics applications such as functional genomics and homology searching.

The term "polypeptide" is used in its broadest sense to refer to a compound of two or more subunit amino acids, amino acid analogs, or peptidomimetics. The subunits may be linked by peptide bonds. In another embodiment, the subunit may be linked by other bonds, e.g. ester, ether, etc. As used herein the term "amino acid" refers to either natural and/or unnatural or synthetic amino acids, including glycine and both the D or L optical isomers, and amino acid analogs and peptidomimetics. A peptide of three or more amino acids is commonly called an oligopeptide if the peptide chain is short. If the peptide chain is long, the peptide is commonly called a polypeptide or a protein.

The term "respiratory syncytial virus" is also referred to herein as "RSV" and includes all strains including, but not limited to, A1, A2, A3, A4, and B. In one embodiment, the RSV virus is an RSV A virus. The RSV can also be modified in some instances by the addition of a fluorescent tag (i.e., RG RSV) or other recombinant methodologies (RA2).

"Selectively binds" refers to a non-specific binding event as determined by an appropriate comparative control. Binding is selective when the binding is at least 10, 30, or 40 times greater than that of background binding in the comparative control.

A "subject," "individual" or "patient" is used interchangeably herein, which refers to a vertebrate, preferably a mammal, more preferably a human. Mammals include, but are not limited to, murines, simians, humans, farm animals, sport animals, and pets.

The terms "treat," "treating," "treatment" and grammatical variations thereof as used herein, include partially or completely preventing, delaying, alleviating, mitigating or reducing the intensity of one or more attendant symptoms of a disorder or condition and/or alleviating, mitigating or impeding one or more causes of a disorder or condition. Treatments according to the present disclosure may be applied preventively, prophylactically, pallatively, therapeutically, or remedially. In some instances, the terms "treat," "treating," "treatment" and grammatical variations thereof, include reducing coughing, sore throat, stuffy or runny nose, earache, or wheezing as compared with prior to treatment of the subject or as compared with the incidence of such symptom in a general or study population. "Treatment" can also be therapeutic in terms of a partial or complete cure for a disease and/or partial or complete cure for an adverse effect attributable to the disease.

As used herein, the terms "prophylactically treat" or "prophylactically treating" refers to treatment that completely, substantially, or partially prevents a disease/condition or one or more symptoms of a disease/condition in a host and/or alleviating, mitigating or impeding one or more causes of a disorder or condition. Similarly, "delaying the onset of a condition" can also be included in "prophylactically treating", and refers to the act of increasing the time before the actual onset of a condition in a patient that is predisposed to the condition.

As used herein, the terms "remedially treating" or "remedial treatment" as well as the terms "therapeutically treat" refer to treatment that completely, substantially, or partially delays, alleviates, mitigates, or reduces the intensity of one or more attendant symptoms of a disorder or condition after infection has been initiated.

DISCUSSION

The present disclosure provides isolated peptides useful for the treatment of respiratory syncytial virus (RSV) as well as methods and compositions for the treatment of RSV infection. In embodiments, the present disclosure describes, peptides useful in the treatment of RSV infection that have increased resistance to protease. In embodiments, HR-derived anti-RSV peptides were designed to form stabilized alpha helical structures. These peptides are able to form fixed coiled-coil structures through disulfide bonding between cysteine pairs located at the N-terminal and/or C-terminal ends. As described in the examples below, peptides were synthesized containing cysteines spaced four or seven amino acids apart. The intrapeptide disulfide bonds that form under oxidizing conditions increase the protease resistances of the peptides.

The present disclosure also provides compositions including micellar nanoparticles that can be filled and/or coated with the isolated peptides of the present disclosure, such as the antiviral HR peptides described herein, to protect them against protease cleavage. The micelle compositions were chosen to facilitate carrying the peptides to the site of RSV infection to block virus entry. The micelles are also able to penetrate target cells where they can deliver the peptides inside the cell. As demonstrated in the examples below, cells treated with peptide-loaded micelles were more resistant to infection than cells incubated with free peptide. Moreover, infected cells treated with micelle formulations showed less susceptibility to propagate infection beyond 24 hours post-infection (pi).

Notably, the peptide HR2-D efficiently inhibited RSV infection in vitro, reducing the virus infectivity by about 80% when administered prophylactically. The stability of the peptide was attributed to the formation of disulfide bonds, with a cysteine at the N-terminus of HR2-D appearing to be relevant to the inhibitory activity of these series of peptides. As described in greater detail below, micelles coated with peptide (MPs) inhibited RSV infection at low and high MOI in Vero and A549 cells. HR2-D-MPs had greater antiviral activity than free peptide in the prophylactic model of infection, but micelles filled and coated with peptide (FMPs) did not appear to demonstrate as effective inhibition when administered therapeutically after infection. FMP reduced infectivity by about 35% compared to positive control.

The next generation of nanoformulations provided herein, modified micelles filled with peptide (FMDs), were successful in reducing the virus infectivity by about 80% when administered under therapeutic conditions. The results show that FM2D are better at protecting the HR2-D cargo and releasing it over a longer period of time, conferring a long-lasting protection as compared to free peptide or FMPs alone. It seems that the negative charge on these nanomicelles helps them to neutralize more effectively the virus interaction with its host. This longer antiviral activity of FM2D could be explained in terms of the negative surface charge of the micelles being attractive to the positive residues on the virus. Thus, when the micelles break, the RSV F protein is readily available to bind to HR2-D. Another reason for the good inhibitory activity of FM2D could be the electrostatic repulsion between the cell membrane and the micelle surface which might keep them in close proximity to the cells and blocking the interaction between the RSV F and its host.

Accordingly, in embodiments, the present disclosure provides isolated anti-RSV polypeptides comprising an amino acid sequence derived from an HR region of RSV F protein, where the polypeptide includes at least one mutation such that the polypeptide sequence includes at least two cysteines spaced about 4 to about 7 amino acids apart, where the cysteines are capable of forming at least one disulfide linkage. In embodiments, the isolated polypeptide sequence includes at least 4 cysteines capable of forming at least two disulfide linkages. In embodiments, the present disclosure provides isolated polypeptides comprising an amino acid sequence comprising, consisting essentially of, or consisting of an amino acid sequence of SEQ ID NO: 2, 3, 4, 5, 6, 7, 8, 9, 10, 11, or 12. These amino acid sequences are provided in Table 1 below. In embodiments, the present disclosure provides isolated HR-derived, anti-RSV peptides including an amino acid sequence comprising, consisting essentially of, or consisting of an amino acid sequence of SEQ ID NO: 2, 4, 5, 6, 7 or 10.

TABLE 1

| SEQ. ID NO. | NAME | SEQUENCE |
|---|---|---|
| SEQ. ID NO.: 1 | HR2 | GSSDEFDASISQVNEKINQSLAFIRRSD ELLHNVNTGKSTTNY |
| SEQ. ID NO.: 2 | HR2-S | FDACISQVNECINQSLAFIRKSDELLHN VNAGKST |
| SEQ. ID NO.: 3 | HR2-E | FDASISQVNEKINQSLAFICKSDELLCN VNAGKST |
| SEQ. ID NO.: 4 | HR2-A | FDACISQVNECINQSLAFICKSDELLCN VNAGKST |
| SEQ. ID NO.: 5 | HR2-B | GISQVNEGKSDELLG |
| SEQ. ID NO.: 6 | HR2-C | GCISQVNECKSDELLCG |
| SEQ. ID NO.: 7 | HR2-D | DACISQVNECINQSLAFICKSDELLCNT |
| SEQ. ID NO.: 8 | HR2-D0 | DASISQVNEKINQSLAFIRKSDELLHNT |
| SEQ. ID NO.: 9 | HR2-D1 | DACISQVNEKINQSLAFICKSDELLCNT |
| SEQ. ID NO.: 10 | HR2-D2 | DACISQVNECINQSLAFIRKSDELLCNT |
| SEQ. ID NO.: 11 | HR2-D3 | DACISQVNEKINQSLAFIRKSDELLCNT |
| SEQ. ID NO.: 12 | HR2-D4 | DASISQVNECINQSLAFICKSDELLHNT |

Embodiments of the present disclosure also include compositions comprising a micelle having a lipid layer and a core, wherein the core includes a first polypeptide, and where the first polypeptide comprises, consists essentially of, or consists of an amino acid sequence selected from the group consisting of: SEQ ID NO:2, SEQ ID NO:4, SEQ ID NO:5, SEQ ID NO:6, SEQ ID NO:7, and SEQ ID NO:10. In some embodiments, the micelle core includes a polypeptide comprising, consisting essentially of, or consisting of the amino acid sequence of SEQ ID NO: 7. In other embodiments, the micelle core includes a polypeptide comprising, consisting essentially of, or consisting of the amino acid sequence of SEQ ID NO: 2.

It should be understood that the micelle lipid layer can include any appropriate lipid composition. In one embodiment, the lipid layer includes or is prepared with amine-PEG-PE (1,2-diacyl-sn-glycero-3-phosphoethanolamine-N-[amino-poly(ethylene glycol)]) as provided, for example, by Aventis Polar Lipids. In other embodiments, the micelle lipid layer includes or is prepared with one or more of amine-PEG-PE, methoxy-PEG-PE (1,2-distearoyl-sn-glycero-3-phosphoethanolamine-N-[methoxy(polyethylene glycol)-2000], and a cationic lipid including, but not limited to, DSPC (1,2-distearoyl-sn-glycero-3-phosphocholine). In still other embodiments, the micelle lipid layer further includes or is prepared with DC-Cholesterol (3β-[N—(N',N'-dimethylaminoethane)-carbamoyl]cholesterol hydrochloride).

It may be preferable in certain applications for the micelle to have a negative zeta potential, and in these applications, the lipid composition is determined accordingly. A negative zeta potential can be achieved by preparing the micelle using one or more lipids such as DSPC and cholesterol. In some embodiments, the lipid is DSPC. It should be understood that the present disclosure includes micelle compositions including one or more HR-derived anti-RSV peptides where the micelle has a zeta potential between approximately −40 and −1 mv, −40 and −20 mv, or −35 and −25 mv. In one embodiment, the micelle lipid layer comprises or is prepared with approximately 20% amine-PEG-PE, 20% methoxy-PEG-PE, and 60% DSPC.

In some embodiments, the micelle also includes a coating, the coating having a second polypeptide that comprises, consists essentially of, or consists of an amino acid sequence selected from the group consisting of SEQ ID NO:2, SEQ ID NO:4, SEQ ID NO:5, SEQ ID NO:6, SEQ ID NO:7, and SEQ ID NO:10. It should be understood that the first and second polypeptides can be the same or different. In some embodiments, the first polypeptide includes or is SEQ ID NO:2 and the second includes or is SEQ ID NO:7.

Embodiments of the present disclosure also include compositions comprising a chitosan nanoparticle and a polypeptide, where the polypeptide comprises, consists essentially of, or consists of an amino acid sequence selected from the group consisting of: SEQ ID NO:2, SEQ ID NO:4, SEQ ID NO:5, SEQ ID NO:6, SEQ ID NO:7, and SEQ ID NO:10.

Also provided herein are methods of using the above-described compositions. These compositions can be used in a method of treating a respiratory syncytial virus infection in a subject, where the method includes administering to the subject a pharmaceutically effective amount of a composition including a micelle having a lipid layer and a core, wherein the core includes a first polypeptide, where the first polypeptide comprises, consists essentially of, or consists of an amino acid sequence selected from the group consisting of SEQ ID NO:2, SEQ ID NO:4, SEQ ID NO:5, SEQ ID NO:6, SEQ ID NO:7, and SEQ ID NO:10.

In some methods, the micelle further includes a coating, where the coating includes a second polypeptide that comprises, consists essentially of, or consists of an amino acid sequence selected from the group consisting of SEQ ID NO:2, SEQ ID NO:4, SEQ ID NO:5, SEQ ID NO:6, SEQ ID NO:7, and SEQ ID NO:10. The first and second polypeptides can be the same or different. In some embodiments, the first polypeptide includes or is SEQ ID NO:2 and the second polypeptide includes or is SEQ ID NO:7.

It may be preferable in certain methods of treatment for the micelle to have a negative zeta potential, and in these methods, the lipid composition is determined accordingly. In some embodiments, the micelle has a zeta potential between approximately −40 and −1 mv, −40 and −20 mv, or −35 and −25 mv. In one embodiment, the lipid layer includes or is prepared with approximately 20% amine-PEG-PE, 20% methoxy-PEG-PE, and 60% DSPC. Further provided is a method of treating a subject by using a micelle having a lipid layer that includes amine-PEG-PE, neutral methoxy-PEG-PE, and DSPC, and a core including a polypeptide of SEQ ID NO:7.

In other method embodiments, the lipid layer includes or is prepared with amine-PEG-PE (1,2-diacyl-sn-glycero-3-phosphoethanolamine-N-[amino-poly(ethylene glycol)]) as provided, for example, by Aventis Polar Lipids. In still other method embodiments, the micelle lipid layer includes or is prepared with amine-PEG-PE, methoxy-PEG-PE (1,2-distearoyl-sn-glycero-3-phosphoethanolamine-N-[methoxy (polyethylene glycol)-2000], and DSPC (1,2-distearoyl-sn-glycero-3-phosphocholine). In still further method embodiments, the micelle lipid layer further includes or is prepared with DC-Cholesterol (3β-[N—(N',N'-dimethylaminoethane)-carbamoyl]cholesterol hydrochloride).

It should be understood that the compositions provided herein can be administered to the subject before and/or after infection with RSV as described above in the Definitions Section. As also described above, such administration can occur in multiple dosages and over an extended period of time.

It should be understood that the foregoing relates to preferred embodiments of the present disclosure and that numerous changes may be made therein without departing from the scope of the disclosure. The disclosure is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present disclosure and/or the scope of the appended claims. It should be further understood that all patents, patent applications, and publications referenced herein are incorporated by reference in their entirety for all purposes.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and protected by the following embodiments.

The following examples are put forth so as to provide those of ordinary skill in the art with a complete disclosure and description of how to perform the methods and use the compositions and compounds disclosed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. In an embodiment, the term "about" can include traditional rounding according to significant figures of the numerical value.

EXAMPLE

Now having described the embodiments of the disclosure, in general, the examples describe some additional embodiments. While embodiments of the present disclosure are described in connection with the example and the corresponding text and figures, there is no intent to limit embodiments of the disclosure to these descriptions. On the contrary, the intent is to cover all alternatives, modifications, and equivalents included within the spirit and scope of embodiments of the present disclosure.

The following examples describe the design and development of protease resistant HR-derived peptides that act as peptide inhibitors of virus particle fusion and the design and testing of multifunctional micellar nanoparticles to deliver the peptide inhibitors.

One of the strategies for preventing RSV infection explored in the following examples includes blockings fusion of the virus particles with host cells by using decoy peptides that specifically bind to the HR2 domain of the RSV fusion (F) protein through coiled-coiled interactions. A series of peptides, 17-28 amino acid residues long were synthesized that contain cysteines spaced 7 residues apart and stabilized by the formation of disulfide bridges. One of these, the HR2-D peptide with two disulfide bonds, was particularly stable and significantly inhibited RSV infection of A549 cells. Further, lipid micellar nanoparticles were used to deliver these peptides to cells. The labeled micelle-HR2-D complex was taken up with an efficiency of >90% by Vero, HEp2 and A549 cells and produced a five-fold reduction in RSV titer (MOI=0.1) compared to free HR2-D. Entry of fluor-tagged RSV (RG RSV) into target cells treated with micelle-HR2-D was significantly reduced (by 80%) 48 h after infection. These results, described in more detail below, demonstrate that HR2-D and related peptides are effective inhibitors of RSV fusion and that micelle-encapsulating peptides have the potential to be used for therapy against RSV infection.

EXPERIMENTAL SECTION

Design and Synthesis of HR2 Peptide Series

HR2 peptides were synthesized by Fmoc solid phase chemistry using 1H-Benzotriazolium 1-[bis(dimethylamino) methylene]-5-chloro-hexafluorophosphate (1-),3-oxide (HCTU) as an activating agent. Peptides containing acid (—COOH) and amide (—$CONH_2$) functionalities on C-terminal were synthesized using Wang and Rink Amide resins respectively. All the syntheses were done at 25 μmole synthesis using Protein Technologies Symphony Peptide Synthesizer. In brief, for each coupling step, 5 equivalents of Fmoc-amino acid and 7.5 equivalents of HCTU are dissolved in 0.4 M N-Methylmorpholine (NMM) in DMF. Fmoc deprotection was done using 20% piperidine/2% DBU in DMF. After the synthesis, the resin was washed with NMP followed by dichloromethane (DCM) and cleaved using cleaving cocktail mixture (94% TFA, 2.5% water, 2.5% ethanedithiol, 1% triisopropyl silane) and precipitated in cold ether. HR2 peptides were purified by reverse phase (RP)-high-performance liquid chromatography using eluting solvents A and B (A=0.1% trifluoroacetic acid (TFA) in water and B=0.1% TFA in acetonitrile).

Anti-RSV peptides were modeled in three dimensions and analyzed for disulfide bond formation using the protein structure prediction software Phyre[2] (www.sbg.bio.ic.ac.uk/phyre2/) and EDBCP (www.biomedical.ctust.edu.tw/edbcp/), respectively.

In order to test the role of disulfide bonding in peptide life-time and anti-RSV activity in vitro, several variants of HR2-S and HR2-D were prepared (HR2-E, HR2-A, HR2-B, HR2-C, HR2-D0, HR2-D1, HR2-D2, HR2-D3, HR2-D4).

Peptide HR2-E has the same number of amino acids as HR2-S, but the two cysteines (19, 26) are positioned at the C-terminal end. HR2-A was also designed using HR2-S as template, but the number of cysteines was increased to four, at positions 4, 11, 19 and 26. HR2-B and HR2-C are shorter versions of HR2-S. HR2-B is 15 residues in length, including residues 5 to 10 and 20 to 25 from HR2-S connected through glycine and flanked by glycines at the N-terminal and C-terminal ends of the peptide. HR2-C consists of 17 amino acids combining residues 4 to 10 and 20 to 26 connected through a cysteine and adding another cysteine after residue 26, thus having 3 cysteines spaced by 7 amino acids and flanked by glycines at the N-terminal and C-terminal ends of the peptide. Lastly, peptide HR2-D was designed as a shorter version of HR2-A of 28 amino acids in length, including residues 2 to 27 and 34 from HR2-A. Thus, HR2-D contains four cysteines at residues 3, 10, 19, and 26, which are predicted to form disulfide pairs from structural prediction models.[12]

Characterization of HR2 Peptides

HR2 peptides were characterized by matrix-assisted laser desorption ionization time of flight mass spectrometry (MALDI-TOF-MS, Agilent 6540 Liquid Chromatography/Quadrupole Time-of-Flight Mass Spectrometer). The peptides in this study were also characterized by circular dichroism (CD, AVIV Model 215 Circular dichroism spectrometer), and the raw data was graphed (data only shown for peptides HR2-S and HR2-D). The samples for CD were prepared by dissolving 0.2 mg of peptide in 1 ml of phosphate-buffered saline, pH 7.2 (PBS).

Preparation of Micelle-Peptide (MP), Filled-Micelle-Peptide (FMP) and Filled-Micelle of HR2-D (FMD) Nanomicelles Synthesis of empty micelles was carried out according to Dubertret et al.[15] Briefly, 3 mg of amine-PEG-PE phospholipid (1,2-diacyl-sn-glycero-3-phosphoethanolamine-N-[amino-poly(ethylene glycol)]) (Avanti Polar Lipids) was dissolved in 1 ml of chloroform. After evaporation of the solvent the pellet was heated to 80° C. and solubilized in 1 ml of nanopure water. HR2-D peptides were then incubated with empty micelles to form MP complexes. Thus, peptides were adsorbed on the surface of the micelles through electrostatic interactions. For the second strategy, FMP were synthesized by dissolving 0.5 mg of peptide in 10 μl of DMSO and sonicating for 5 min to ensure homogeneous dispersion. Next, the peptide in DMSO was mixed with lipids in the same fashion as for making empty micelles. Finally, the peptide-loaded micelle was further incubated with HR2-D peptide for 2 h at room temperature, resulting in FMP. For therapeutic experiments, filled micelles containing HR2-D (FMDs) were prepared by dissolving 0.2 mg of HR2-D in a mixture of 10 μl of DMSO+10 μl of triethylamine and dried on a glass vial. Later the peptide in DMSO/triethylamine was combined with a mixture of lipids containing 4 kinds of lipids at 4 different ratios. The four formulations of FM-HR2-D were named as follows—FM1D, FM2D, FM3D, and FM4D. FM1D contained 10% amine-PEG-PE phospholipid (1,2-diacyl-sn-glycero-3-phosphoethanolamine-N-[amino-poly(ethylene glycol)]), 10% methoxy-PEG-PE (1,2-distearoyl-sn-glycero-3-phosphoethanolamine-N-[methoxy(polyethylene glycol)-2000], 40% DSPC (1,2-distearoyl-sn-glycero-3-phosphocholine), 40% DC-Cholesterol (3β-[N—(N',N'-dimethylaminoethane)-carbamoyl]cholesterol hydrochloride) in chloroform (Avanti Polar Lipids). FM2D was prepared with 20% amine-PEG-PE, 20% methoxy-PEG-PE, 60% DSPC. FM3D was prepared using 10% amine-PEG-PE, 10% methoxy-PEG- PE, 25% DSPC, 55% Cholesterol. FM4D contained a mixture of 8% amine-PEG-PE, 8% methoxy-PEG-PE, 54% DSPC, 30% cholesterol in chloroform. The micelles were prepared following the same strategy as described for empty micelles. Non-encapsulated peptide was removed by centrifugation (4000×g) and resuspended in 1 ml water after using a 30K MWCO membrane.

Labeling of Amine-Coated Micelles and HR2-D Peptide with Mono NHS-Cy5 Dye

HR2-D peptide or micelles was labeled with mono NHS-Cy5 (GE-Healthcare) using coupling chemistry between amine groups (on the peptide or on the micelle) and NHS group of the dye.[16] Typically, NHS-Cy5 was added to HR2-D or micelle dissolved in water (at 1 mg/ml for HR2-D or 3 mg/ml for micelle) at a molar ratio of 5:1 (dye to amine) and incubated for 2 h at room temperature. Excess Cy5 dye was removed by dialysis overnight against water using a cellulose membrane of 1K MWCO for peptide and centrifugation (4000×g) for 1 h using a 100K MWCO for micelles. Labeled micelles were used for uptake experiments with flow cytometry. The labeled HR2-D peptide was used for encapsulation into the micelle core and testing for RSV infection inhibition in therapeutic studies.

Characterization of MP, FMP and FMD Micelles

The hydrodynamic radius of functionalized micelles (FMDs), micelle-peptide complexes (MPs), FMP, Cy5-amine-coated micelles and Cy5-HR2-D in water was measured using dynamic light scattering and zeta potential (DLS, Microtrac). Aliquots for DLS were prepared by diluting the stock samples 1:5, passing them through a 0.2 μm syringe-filter and sonicating for 10 min to disrupt aggregation.

DOX release studies on FMDs were done using confocal microscopy. For confocal imaging, 50K cells (LLC1) were placed on a fluorodishes and grown overnight before treatment with FMDs of DOX (3 μg conc./dish) and incubated for different time points (4-24 h) at 37° C. Cells were placed in a live-cell environmental chamber at 37° C. with 5% $CO_2$ and imaged using spinning-disk confocal microscopy (Olympus IX81 confocal microscope). Uptake was quantified by ImageJ statistical analysis software.

RSV Preparation and Cell Culture

Growth and titration of the respiratory syncytial virus (RSV) strains A2, RG RSV (green-fluorescent tag), and rA2 were performed as previously described in the literature.[17,18] RSV was propagated in HEp-2 cells containing 0.1 PFU/cell in T-175 flasks supplied with 7 ml of 2% FBS, OptiMEM (virus yield $10^6$-$10^7$ pfu/ml). Infection was allowed for 2 h. (at 37° C., 5% $CO_2$) and then replaced with fresh media. The infection was allowed to progress until CPE (80-90%), typically happening after 3 days of incubation. Viral suspension was collected and combined with scrapped cells in to a vial and centrifuged at 3200 rpm for 10 min at 4° C. The culture supernatant was collected and mixed with 0.1 volumes of sterile magnesium sulfate (1M). Last, viral supernatant was stored in cryovials and stored in liquid nitrogen tank.[18,19] Viral titers were measured using carboxymethylcellulose plaque assay on HEp-2 cells grown to 80-90% confluency at 5% FBS/DMEM in a 24-well plate (70K cells per well).[17,18,19] Virus particles were visible and quantitated after immunochemistry treatment of the cells with primary anti-RSV F mouse monoclonal [RSV3216 (B016)] (1:1000 dilution) and secondary antibody against primary with HRP conjugate.

RSV-susceptible cell lines such as Vero, HEp2 and A549[17] were used for studying the micelle-peptide activity. Prophylactic studies were carried out administering the micelle-peptide formulations previous to infection while therapeutic experiments were performed giving micelle-peptide dose after infection. Typically, Vero and HEp2 cell lines were grown in DMEM with 5% FBS and A549 and HEK 293 was cultured in DMEM supplemented with 10% FBS plus 1% penicillin/streptomycin (P/S), respectively. All cell lines were maintained in an incubator at 37° C. in the presence of 5% $CO_2$. Cells during RSV infection experiments were grown in DMEM without FBS or P/S in 24 or 48-well plates.

Labeling of FM2D with FITC and Mono NHS-Cy5 Dye and A2 RSV with R18 (Octadecyl Rhodamine B Chloride)

0.5 mg of HR2-D was added to 0.5 mg of FITC in DMSO and incubated overnite at 4° C. Labeled peptide was encapsulated inside the micelle according to previously described FM2D preparation. Excess dye was removed by dialysis (10K MWCO) against nanopure water for 8 h at 4° C. (process repeated two times). FM2D containing FITC was further conjugated with Cy5 in same way as described in the amine micelle labeling step. 300 μl of A2 RSV (1.6 $e^7$ pfu/ml) was mixed with 50 μl of R18 stock solution (0.1 μg/μl) for 1 h at 4° C. After incubation, excess dye was removed using macro spin column (75-150 μl, Harvard Apparatus). Labeled virus was stored at −20° C.

Prophylactic Model of Treatment Against RSV Infection

25K Vero or A549 cells grown in 48-well plates and supplied with DMEM (no serum) were treated with a dose of peptides or micelle-peptides (5 μM peptide/well) for 30 min. previous to infection with RSV. Infection was carried out at a 0.1 MOI and allowed in the cell culture for 1 h. After removal of viral supernatant, the cells were treated with a second dose of peptides or peptide-loaded micelles containing 5 μM peptide/well in DMEM (5% FBS, 1% P/S). Infection was followed for a period of 48 h through microscopy and quantified through flow cytometry.

Therapeutic Model of Treatment Against RSV Infection

25K A549 cells grown in 48-well plates and supplied with DMEM (no serum) were infected with RSV at a 0.1 MOI for 1 h. After washing the viral supernatant, cells were incubated in DMEM (5% FBS, 1% P/S) allowing progression of infection for different time periods (4 and 24 h), however, only 24 h is shown here. At these two time points, cells were treated with a dose of peptides or micelle-peptides containing 5 μM peptide/well. Infection was followed for a period of 48 h through microscopy and quantified through Image J statistical analysis software.

RSV Infection and Molecular Biology Characterization: Inverted Fluorescence Microscopy, Plaque Assay Analysis, Confocal Microscopy and Flow Cytometry The effect of inhibitory peptides (HR2-A, HR2-B, HR2-C, HR2-D, HR2-E, HR2-S, HR2-D0, HR2-D1, HR2-D2, HR2-D3, HR2-D4) on RG RSV infection given by prophylactic method was visualized by inverted fluorescence microscopy (Olympus IX371) and quantitated by flow cytometry. For plaque assays, 50K HEp2 cells/well were seeded in 24-well plates and infected with RG RSV (0.1-1 MOI) in the presence of peptides for 1 h. The viral supernatant was removed and a second dose of peptides in methylcellulose/5% FBS was overlaid onto the cells. Plaques were visualized and quantified (3-5 days pi). Cellular uptake was characterized using confocal microscopy and flow cytometry. For confocal imaging, 50K cells (Vero, A549) were placed on a fluorides and grown overnight before treatment with MPs (5 μM peptide conc./dish) and incubated for 1 h at 37° C. Cells were placed in a live-cell environmental chamber at 37° C. with 5% $CO_2$ and imaged using spinning-disk confocal microscopy (Olympus IX81 confocal microscope). Uptake was quantified by flow cytometry (BD FacsAria analyzer/sorter). Samples for flow cytometry were prepared using 50K cells/well seeded in 24-well plates and grown in DMEM plus 10% FBS and incubated with peptides at a concentration of 5 μM peptide/well for 30 min at 37° C. Treated cells were infected for 2 h with RG RSV (green-fluorescent, 0.2 MOI) or RSV strain RA2 (0.2 MOI) followed by washing and incubated with fresh media containing peptides with 5 μM peptide/well overnight. Flow cytometry samples were prepared 24 h and 48 h pi. Similar protocol was followed for infected cells containing MPs and FMPs for preparing flow cytometry samples. Final cell pellet was suspended in 400 μl of 1×PBS and analyzed for green and/or red content.

Statistical Analyses

Figure 2:
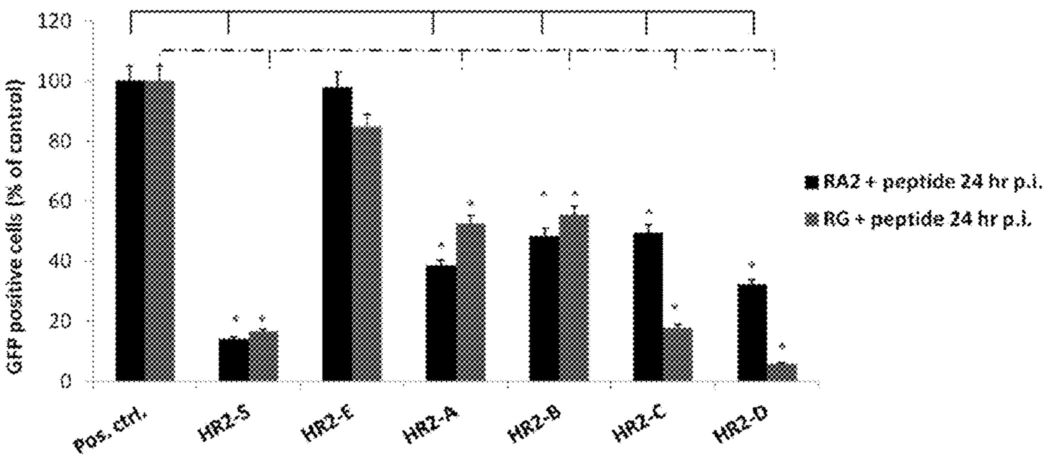
FIG. 2 is a bar graph illustrating the effect of HR2 peptides on RSV entry and replication. Flow cytometry of HEp2 cells incubated with various peptides then infected with RSV RA2 or RG RSV. Significant P values (P<0.01) are shown as * where it corresponds. Each treatment was compared individually to the positive control for each virus strain tested: solid line indicates comparison with respect to RA2 RSV control and dotted line indicates comparison with respect to RG RSV.
Figure 3:
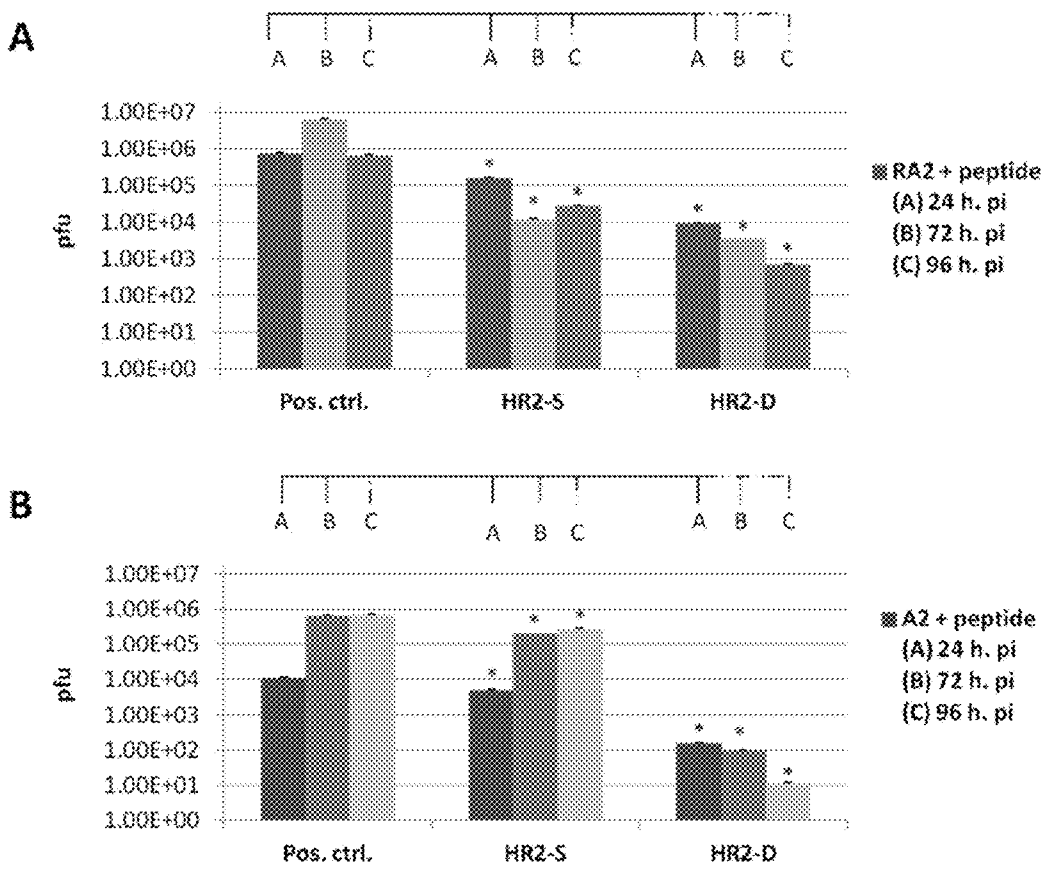
FIGS. 3A and 3B are bar graphs illustrating RSV titers from cells infected with RA2 RSV (FIG. 3A) and A2 RSV strains in presence of peptide HR2-S (one disulfide) or HR2-D (two disulfides) (FIG. 3B). Significant P values (P<0.01) are shown as * where it corresponds. Each treatment was compared individually to the positive control for each virus strain tested; solid lines (24 h pi), dotted lines (48 h pi), or broken lines (96 h pi).
Figure 8:
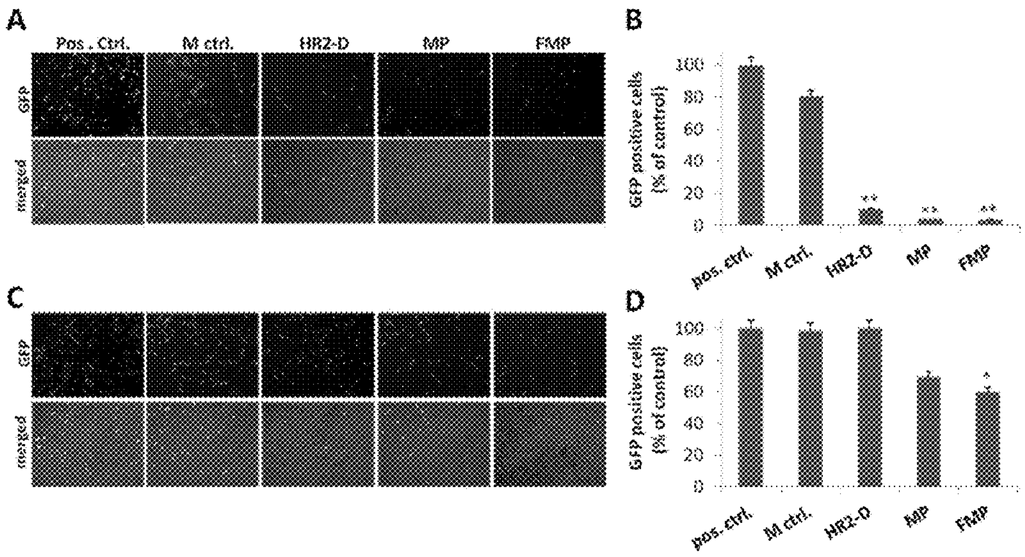
FIGS. 8A-8D are digital images and bar graphs illustrating prophylactic (FIGS. 8A-B) and therapeutic (FIGS. 8C-D) antiviral activity of MP and FMP in A549 cells infected with RG RSV. Each treatment was compared individually to the positive control RG RSV infected cells. In case of prophylactic model significant results are denoted by ** and in therapeutic model by *. Significant P values (P<0.01) are shown as ** or (P<0.05) * where it corresponds.
Figure 10:
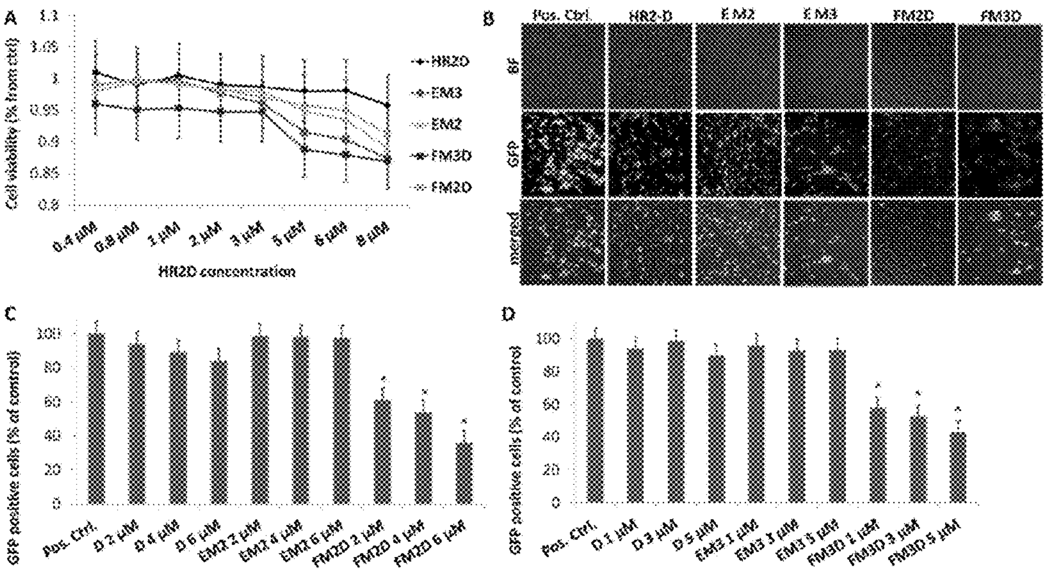
FIG. 10A is a graph illustrating the cytotoxicity of FM2D and FM3D in A549 cells treated for 72 h.
FIG. 10B is a series of digital images illustrating the therapeutic antiviral activity of FMDs in A549 cells infected with RG RSV via confocal microscopy of infected cells 48 h pi. EM2 and EM3 represent empty micelle control.
FIGS. 10C-10D are graphs illustrating quantitative analysis by flow cytometry; significant P values (P<0.05) are shown as * where it corresponds. EM2 and EM3 represent empty micelle control.

All statistical analyses were performed using Graphpad Prism 5.03. GFP expression levels from flow shown in FIG. 2 was performed in duplicate and repeated two times. The GFP expression axis (left axis) was labeled according to the ratio of the mean average of a given treatment with respect to the mean average positive control value. The P values were calculated for each peptide treatment and compared with respect to positive control for each virus strain tested individually. Significant $P<0.01$ values are denoted by * where it corresponds. Viral titers shown in FIG. 3B were measured in triplicate, and the mean average value is shown. P values were calculated using the mean values and the s.e.m. values. Significant values ($P<0.01$) were reported by an asterisk (*). Flow cytometry results from cells treated in a prophylactic model with HR2-D peptide series and HR2-S is shown in FIG. 3. The GFP expression levels were averaged from two independent experiments. P values were calculated and reported when they were found significant ($P<0.05$). Flow cytometry results from cells treated in a prophylactic and therapeutic model with HR2-D, MPs, or FMPs is shown in FIGS. 8B and 8D, respectively. The GFP expression levels were averaged from three independent experiments run in duplicate. P values were calculated and reported when they were found significant ($P<0.01$, in case of FIG. 8B and $P<0.05$, in case of FIG. 8D). Statistical analysis results from cells treated in therapeutic model with HR2-D or FMDs is shown in FIGS. 10C and 10D. The GFP expression levels were averaged from two independent experiments run in duplicate. P values were calculated and reported when they were found significant ($P<0.01$).

Live Cell Imaging of FM2D and R18 Labeled A2 RSV in A549 Cells

50 K A549 cells were plated on a fluorodish and grown overnight in 10% FBS serum. Confocal imaging was performed on an Olympus IX81 inverted microscope equipped with the 3i Yokogawa spinning disk scanner and CCD cameras. Three wavelengths (488 nm, 561 nm and 640 nm) were selected to image the interaction of FITC labeled HR2-D, R18 labeled A2 RSV and Cy5 labeled FM2D with A549 cells. Cell membranes were unstained due to the interference of fluorescent signal from stained cell membrane and the virus or FM2D colocalization events at the cell membrane. FM2D and the virus were incubated for 15 min at RT before adding it to the cells. The images were taken in a 10 min interval for a period of 6 h after treatment. Cells were kept alive in a cell environmental chamber that maintains the temperature and $CO_2$ level constant while imaging. The images were analyzed using Slidebook 5.0 software.

In Vivo Model of RgRSV Infection and Intranasal Prophylactic Treatment.

Ten week old BALB/c mice (n=4 per group) were anesthetized and treated intranasally with the indicated HR2D peptide (125 μM in 1.2% DMSO) or packaged in filled micelles or with chitosan nanoparticles and empty micelles control. One hour post reatment, three groups of mice were inoculated with a single dose of rgRSV at $1\times10^6$ pfu/mouse. Mice were sacrificed at 24 hours post infection and the noses harvested, sectioned, stained with DAPI and imaged for GFP using an Olympus fluorescent microscope.

Results

A series of anti-RSV peptides with helical structures and stabilized by various numbers of cysteines (FIG. 1A, FIG. 4A) was synthesized and tested for inhibition of RSV infection in vitro to determine if the presence of specifically placed disulfide bonds increases the half-life of the peptides by reducing proteolytic cleavage. Disulfide bridging provides a simpler alternative to the stabilization of synthetic peptides by stapling chemistry.[12] Inhibitory peptides were designed using the heptad repeat HR2 (SEQ ID NO: 1) of the RSV F protein as template, and replacing few amino acids with the introduction of 2-4 cysteines spaced 7 residues apart. The helical structure of the HR2 peptide series was predicted using the Phyre[2] modeling software, as shown in FIG. 1B for HR2-S and HR2-D and confirmed by circular dichroism (CD) in FIG. 1C. Two inflection points appeared around 208 and 220 nm, a typical sign of α-helical conformation.[20,21]

The anti-RSV activity of peptides HR2-S, HR2-E, HR2-A, HR2-B, HR2-C, and HR2-D was tested in vitro following a prophylactic model of RSV infection in HEp2 cells described in the experimental section above. RG and RA2 RSV strains were used to quantify infection by flow and RA2 and A2 strains were used to quantitate the viral titers by immunochemistry. HEp2 cells were incubated with the peptide then infected with RG RSV (RG) or RSV RA2 (RA2). At 24 h after infection, GFP expression levels were compared for cells infected with RG RSV and FITC-labeled anti-RSV staining for cells infected with the RA2 RSV strain. The antibody used to detect RSV antigens expressed on the RA2 infected cells was mouse derived RSV FITC-labeled monoclonal antibody 5022 (Chemicon International), FIG. 2.

Following the same methodology as for flow, two doses of peptides were used, and virus inoculation was 0.2 MOI. Titers were quantified 24 to 96 h after infection (pi). At 24 h to 96 h pi, A2 viral titers were not significantly reduced by HR2-S (about 0.2 fold reduction), in contrast to HR2-D where a 100-fold or greater reduction in titers occurred for both RA2 and A2 (FIGS. 3A and 3B). RA2 titers showed a 100-fold decrease in HR2-S- and HR2-D-treated cells. A2 showed 0.1 fold decrease for HR2-S treated cells while a 100 fold reduction of infection was observed for HR2-D treated cells. The last time point recorded was 96 h pi, again the same pattern as for 72 h was observed for RA2 and A2 infected cells. RA2 titers were 20 fold smaller for HR2-S and 1000 fold less for HR2-D. In case of A2 titers, a 0.1 fold decrease was observed in HR2-S treated cells while a 50,000 fold reduction was counted for HR2-D treated cells.

Figure 4:
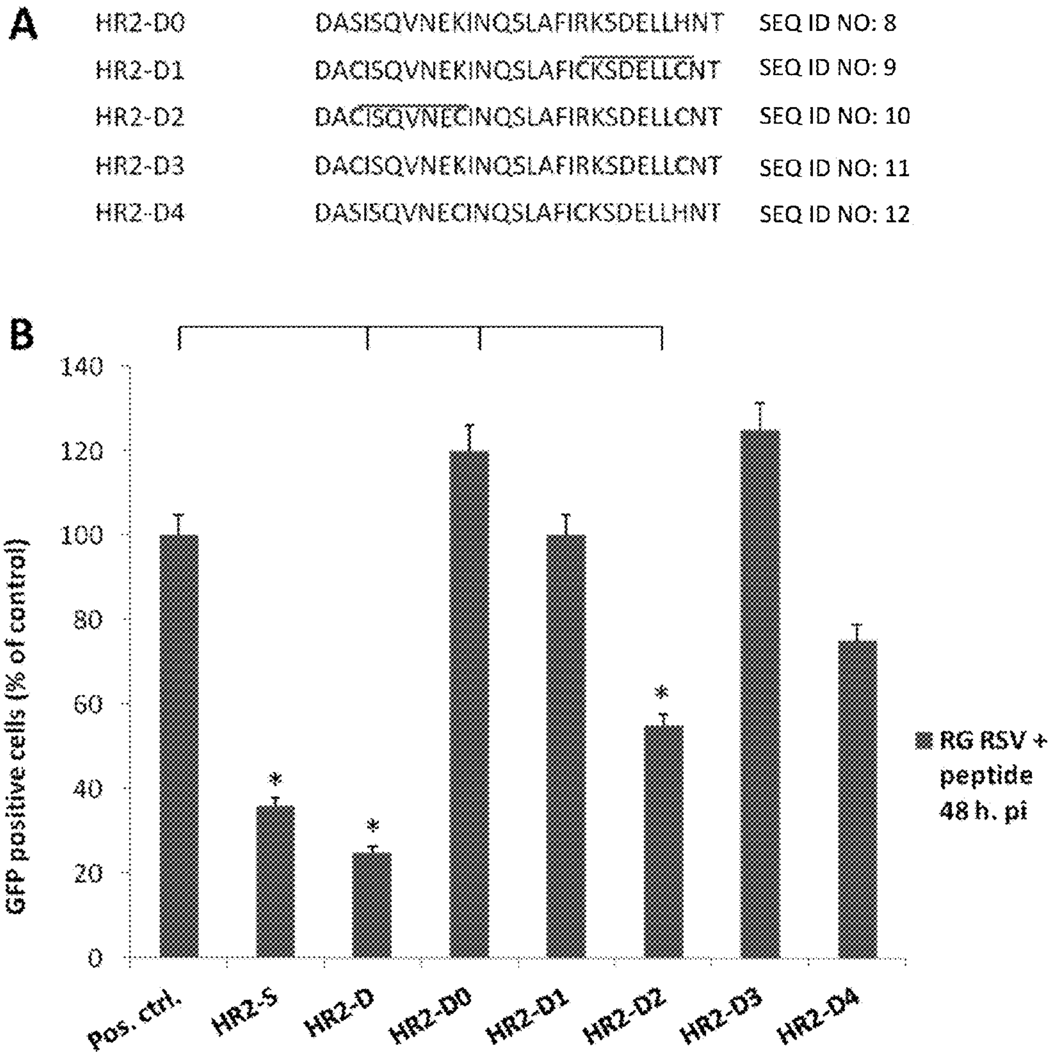
FIG. 4A illustrates the amino acid sequences of an HR2 series of synthetic peptides (SEQ ID NOs: 8-12), over-line indicates disulfide linkages.
FIG. 4B is a bar graph illustrating the effect of number and position of disulfide bonds in HR2-D peptides and their anti-RSV activity by flow cytometry. Significant P values (P<0.05) are shown as * where it corresponds. Each treatment was compared individually to the positive control with respect to RG RSV infection.

Since the RSV titer data with HR2-S and HR2-D did not follow a single pattern, a new set of peptides was designed. The second set of peptides (HR2-D0-4, SEQ ID NOS: 8-12, FIG. 4) was used to determine the role of disulfide bonding in RSV inhibition, and to confirm that the predicted pairs (between amino acids 3 and 10, and 19 and 26) were indeed forming. HR2-D0 is a control peptide with no cysteine. It contains residues 7 to 33 from the original HR2 peptide and a Thr at position 34 instead of Val. HR2-D1 is identical to HR2-D except that the cysteine at position 16 was replaced by Lys, disrupting the formation of a bond between cysteine 9 and 16. HR2-D2 contains 3 cysteines at positions 9, 16, and 32, thus disrupting the bridge between cysteine 25 and 32 located at the C-terminus. Two more peptides, HR2-D3 and HR2-D4 containing only 2 cysteines were also synthesized (FIG. 4A).

Infection experiments with the HR2-D series were carried out in Vero cells following a prophylactic model of infection using RG RSV (MOI=0.1) strain. At 48 h after infection, the cells were analyzed for GFP (positive RSV infection) by flow cytometry. HR2-D0, which has no cysteine, did not show any inhibitory activity against RSV infection. HR2-D1 looks similar to the positive control. Compared to HR2-D0, HR2-D1 is about 30% lower. For the activity of the inhibitor peptide HR2-D (~20% GFP from positive control), as shown by the loss of activity by 1.5 fold for HR2-D2 vs. 2.5 fold for peptide HR2-D1. Moreover, the presence of the one free cysteine which is not forming a disulfide bond might result in destabilizing the whole structure. HR2-D1 and HR2-D2 have a free cysteine residue at position 9 and 32, respectively while HR2-S, HR2-D3 and HR2-D4 contain only one pair of cysteines. However, the activity of HR2-D3 was 3-fold less compared to HR2-S (~38% GFP from positive control), while HR2-D4 was 2-fold less effective in blocking infection (FIG. 4B).

Therefore, after successful identification of candidates for RSV treatment, the next step was to improve its stability and activity by conjugation to biocompatible drug delivery systems. The choice of carrier was PEG-functionalized phospholipid micelles since they are small in size (<50 nm in diameter), are biocompatible (phospholipids mimic cell membrane environment and PEG decreases unspecific binding), and can be easily functionalized (positive, negative, or neutral charged groups) to bind to a variety of molecules such as peptides.

Figure 5:
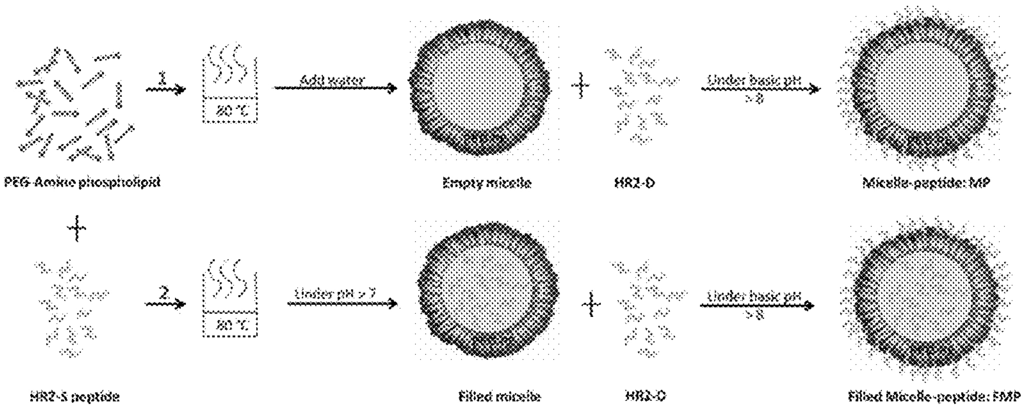
FIG. 5 is a schematic illustration of the MPs and FMPs nanoparticles self-assembly model. Scheme 1 (upper) corresponds to the assembly of MPs and Scheme 2 (lower) illustrates the assembly of FMPs.

According to the first scheme in FIG. 5 (upper), empty micelles are formed by melting the lipids above their transition temperature followed by the addition of water. Later, peptides were adsorbed onto the amine-functionalized micelle surface to form micelle-peptide complexes (MPs) that can gradually release the peptide over an extended period. The highly polar HR2-D binds to the positively charged amine groups on the micelle exterior and takes longer to be released into the medium due to electrostatics. There is equilibrium of HR2-D due to competition between its electrostatic affinity to the micelle and its coiled-coil interactions with the HR2 domain of RSV F.

In the second scheme (FIG. 5, lower), the micelle carrier was further functionalized by filling the interior as well as the exterior with peptides to create filled micelle-peptide complexes (FMPs). Since the interior of the micelles is hydrophobic and the exterior hydrophilic, two different peptides were used: peptide HR2-S(SEQ ID NO: 2), which is less water soluble for the core and HR2-D (SEQ ID NO: 7) for the surface. HR2-S has several polar side-chains (Asp, Lys, Arg) and it is not compatible with hydrophobic solvents such as chloroform, used to dissolve the lipids. In order to change the solubility and the hydrophobicity of HR2-S, it was dissolved in a mixture of 1:1 DMSO: $CHCl_3$. In this approach, hydrophobic HR2-S and lipids are dissolved in chloroform, dried and heated till melting is observed. Addition of aqueous buffer results in the formation of filled micelles, termed as FMPs. Later, functionalization of the micelle exterior was done using same strategy as in first scheme. As previously reported in the literature,[16,22,23] filling the core of these micelles makes them more resistant towards degradation, and it can protect its cargo (in this case, anti-RSV peptides) for a prolonged time, an important asset for an effective treatment against viral infections.

Figure 6:
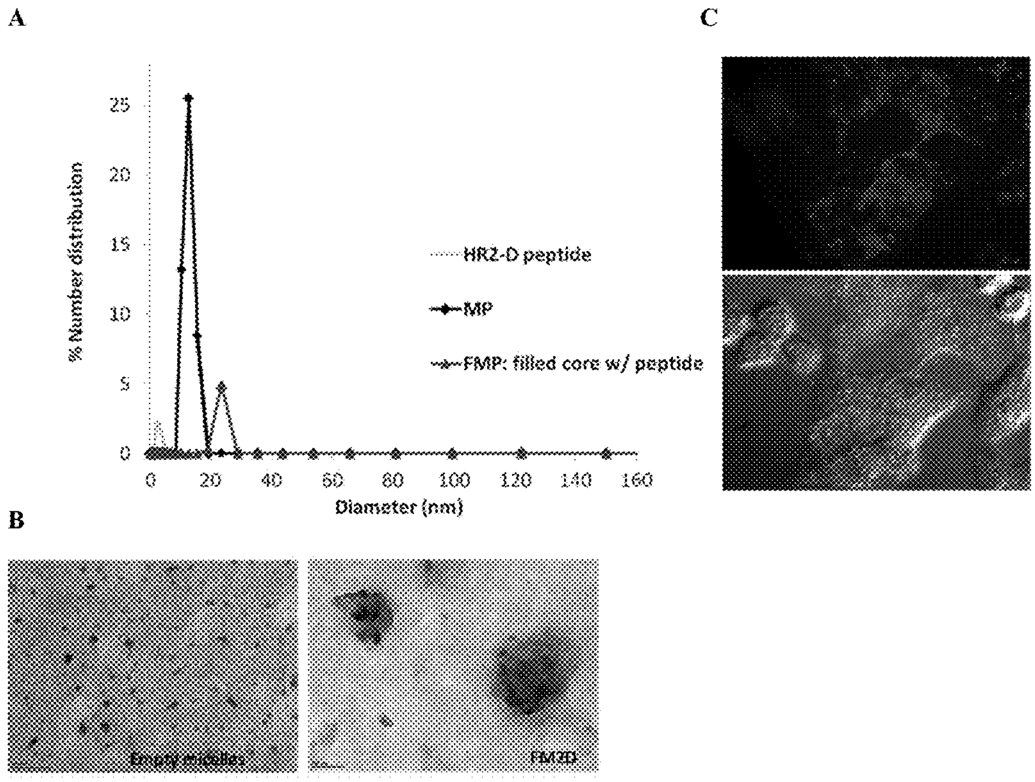
FIG. 6A is a graph illustrating the hydrodynamic diameter of MPs, FMPs and peptides measured by DLS.
FIG. 6B shows electron micrograph of empty and filled micelles.
FIG. 6C is a pair of digital images of illustrating cellular uptake in Hep-2 cells using Cy5 labeled MPs and treated for 4 h before imaging.
Figure 7:
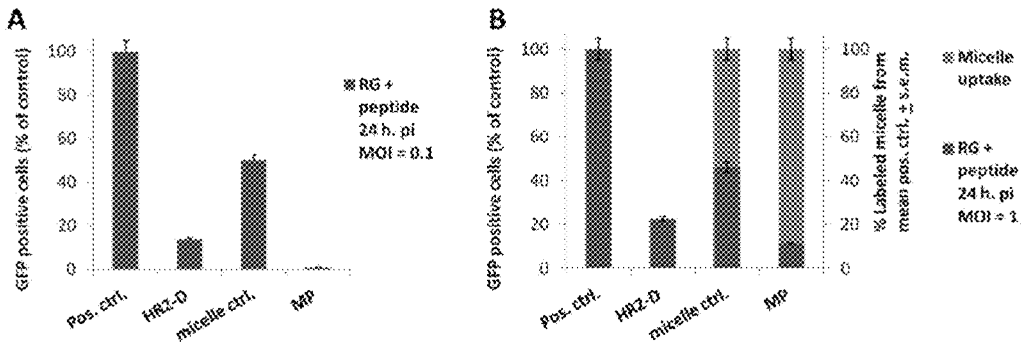
FIGS. 7A-7B are bar graphs illustrating flow cytometry results showing that MPs are efficiently internalized by Vero cells at low virus concentration as well as high concentration. Light gray bars display the uptake of labeled MPs by Vero cells at high MOI.

The hydrodynamic diameter of micelles with surface-conjugated peptides (MPs) was measured and compared to MPs with peptides also in the core (FMPs) (FIG. 6A). HR2-D peptide in aqueous solution is 2 nm in diameter and after conjugation to the micelle surface, the MP is 15.5 nm. In order to test the ability of MP and FMPs to carry their cargo to the cell membrane where RSV F interacts with the host receptors, uptake experiments were performed using labeled MPs (FIG. 6B). FIG. 6B shows the successful localization and internalization of the micelles into HEp2 cells after being treated for 1 h with the Cy5 labeled MPs. Subsequently experiments involved using Cy5 labeled peptides conjugated to the micelles and quantifying its activity against RG RSV infection by flow cytometry. To obtain a clear distinction of the cell population that was infected with RG RSV and expressing GFP from the residual fluorescence signal coming from Cy5 labeled cells, which also contributed to the green fluorescence, controls were run with cells stained only with Cy5 and the contribution of red channel into the green channel gate was gated out. In addition, DAPI was added to distinguish between dead cell populations from live cells during gating. FIG. 7A shows that at low MOI (0.1) the infection in Vero cells is blocked by 95% with MPs of HR2-D administered in a prophylactic model and measured after 24 h pi, as compared to the positive control.

The red channel was gated to quantify the population of Cy5-labeled cells from the total parent. It is interesting that Cy5-labeled micelles alone are capable of neutralizing the infection by about 40%. HR2-D blocked the infection by 85% as seen before in other cell lines (HEp2) at 24 h pi. Moreover, the inhibition capacity of HR2-D and MPs of HR2-D was tested against higher MOI (1) in Vero cells and analyzed by flow after 24 h. (FIG. 7B). MPs of HR2-D showed the best activity, decreasing the GFP levels by 2.5 fold less (left axis) than HR2-D alone. MPs also showed efficient uptake (right axis, >90%) in the two cell lines tested (HEp-2, Vero). Only Vero cells are shown in FIG. 7B.

Since MPs inhibited RSV infection when the HR2-D was administered prophylactically, MPs were next tested in a therapeutic model of RSV infection again comparing free HR2-D to HR2-D-MPs and also introducing FMPs of HR2-S and HR2-D in the study. For these experiments FMPs were used since micelles are easy to internalize and carry their cargo inside cells. If FMPs slowly break down in the cells and release the HR2-S, it limits the formation of virus progeny by interactions with F protein. Parallel experiments were done using A549 cells incubated with FMPs either before or after infection with RG RSV. In the prophylactic model of infection (FIGS. 8A and 8B), peptide or FMPs were added to A549 cells and infected with low virus concentration (MOI=0.1). RG RSV infected cells were imaged, and RSV-positive cells were counted by measuring GFP expression using flow cytometry (FIG. 8B). In parallel, A549 cells were infected with RG RSV (MOI=0.1) and treated with FMPs and peptides following the therapeutic model. Treatment was given to infected cells 4 h. pi and analyzed after 24 h by microscopy and flow cytometry (FIGS. 8C and 8D).

In the prophylactic model, FMPs reduced significantly virus infection ($P<0.01$) by 8 fold compared to free HR2-D (not significant, $P>0.05$) and neutralized the GFP expression by 90% with respect to the positive control, similar inhibition was shown for MPs ($P<0.01$), FIG. 8B. However MPs did not show significant inhibitory activity ($P>0.05$, 40% neutralization) administered in the therapeutic model (FIG.

8D) compared to positive control. FMPs appeared more successful in blocking infection compared to MPs ($P<0.05$, 50% neutralization).

Moreover, the FMPs inhibited infection in same degree as MPs in the prophylactic model (by 90%) as well as in the therapeutic model (by 50%) (FIGS. 8B and 8D). However, FMPs had a significant effect on GFP expression, decreasing it to half as compared to positive controls. The flow cytometry data was corroborated by microscopy (FIGS. 8A and 8C).

Improved FMDs micelles were prepared using a mixture of lipids that facilitate the release of the core contents. Thus, cationic lipids (DC-Cholesterol, DSPC) were introduced in the micelle composition, in addition to amine-PEG-PE, and neutral methoxy-PEG-PE. Four different core-filled micelles were prepared with different ratios of the lipid components described in experimental section above: FM1D, FM2D, FM3D, and FM4D.

FIG. 9A illustrates the steps involved in the preparation of mixed-lipid micelles of HR2-D and its characterization by dynamic light scattering and zeta potential, shown in FIGS. 9B and 9C, respectively.

The hydrodynamic size of FM1D and FM3D is 28 and 29 nm, respectively (FIG. 9B). FM1 D has +39 my charge on its surface while FM3D has +40 my surface charge. On the other hand, FM4D was prepared with lower cholesterol content (30%) in order to have less rigidity and still keep positive charge. FM4D micelles had the smallest size measuring 22 nm in diameter. The zeta potential of FM4D revealed a weakly positively charged surface of +12 my correlating with lower cholesterol amount. FM2D was another formulation with no cholesterol but high DSPC content; the hydrodynamic diameter of FM2D was 35 nm. Consistent with the direct relation between DC-Cholesterol content and positive surface charge, the zeta potential of FM2D was highly negatively charged, −30 my.

For testing the efficiency of FMDs, cytotoxicity was measured in A549 cells at different HR2-D peptide concentrations using FM2D and FM3D, respectively (FIG. 10A). EM2 and EM3 represent empty micelle control. A549 cells were infected according to therapeutic conditions, and FMD (6 μM FM2D, 5 μM FM3D) were administered 24 h pi. The images were visualized 48 h pi (FIG. 10B) and the inhibitory efficiency quantified using flow cytometry (FIGS. 10C and 10D). HR2-D alone, administered in therapeutic conditions, did not control the infection significantly ($P>0.05$) compared to the positive control, as shown above (FIG. 8D). Moreover, FM2D was successful in reducing the GFP levels by 80% as compared to the positive control, and it was twice more efficient than FMPs (FIG. 8D). FM3D had good inhibitory activity by suppressing the expression of GFP by 65% as compared to the control.

Figure 11:
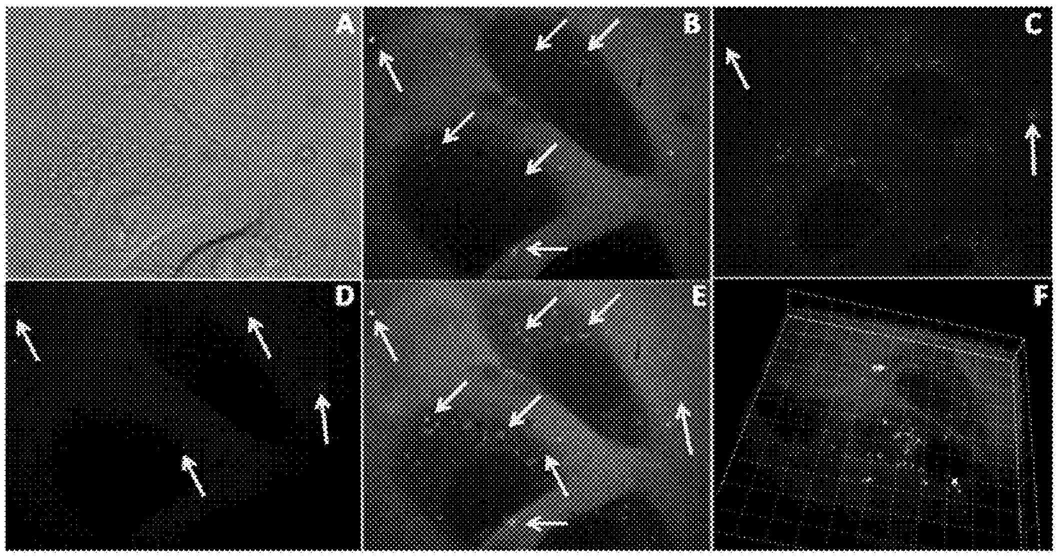
FIGS. 11A-F are a series of digital images including a brightfield image of three cells showing the nucleus (11A), internalization of green labeled peptide inside the cells (white arrows (11B)), RSV infection taking place on the cells (yellow arrows depict colocalization of peptide and empty micelles with virus) (11C), imaging of labeled micelles interacting with the cell membrane as well as blocking virus entry in the vicinity of the cells (yellow arrows indicate micelle attachment on the cell membrane and colocalization with virus) (11D), merged image of the three channels (yellow arrows show colocalization of peptide with virus inside the cells, peptide inside micelles with virus) (11E), and 3D volume image of representing the interaction of peptide and micelles with the virus (11F).

In order to evaluate the inhibitory efficiency of FM2D on infected A549 cells, confocal microscopy was carried out using labeled peptide, micelle and virus. FIG. 11 illustrates the colocalization events of micelles, FM2D with labeled virus.

To determine if the in vitro anti-RSV activity of HR2D translated to an in vivo context, in vivo testing was performed on mice. HR2D peptide itself, HR2 peptide with filled micelles, empty micelles as control, and HR2D peptide chitosan nanocomplexes were each administered by nasal drop (50 μL of 125 μM solution in 1.2% DMSO) to ten week old BALB/c mice followed by intranasal inoculation with a single dose of rgRSV ($1\times10^6$ pfu) one hour later. Mice were sacrificed 24 hours after infection, and the noses harvested, sectioned, stained with DAPI, and subjected to fluorescence imaging. The microscopic images demonstrated a marked reduction in GFP-positive nasal tissue in HR2D peptide treated mice compared to empty micelle control. Further, HR2D-filled micelles and chitosan nanocomplex treated mice showed no RSV infection as evaluated by green fluorescence. Thus, we find that pretreatment of rgRSV-infected mice with intranasal HR2D peptide markedly decreases nasal infection.

DISCUSSION

This example describes the development of a novel peptide-based inhibitor for RSV infection by incorporating alpha-helix stabilized peptides with a micellar nanoparticle. The design of the therapeutic RSV drug delivery system involved several steps: i) the synthesis and characterization of helical peptides targeting the HR2 domain of the fusion protein of RSV, ii) the selection of peptides with antiviral activity against RSV infection, iii) the preparation of the biocompatible nanocarrier delivery system based on PEG functionalized phospholipid micelles, and iv) the quantification of the inhibitory activity of micelles loaded with peptides administered before or after RSV infection at low and high virus concentration. The structural conformational changes of HR peptides of RSV fusion protein during fusion and post-fusion are characterized. Previous reports in the literature have shown that small drugs have successfully interfered with the post fusion conformation of HR1 and HR2 domains, thus blocking viral entry into the host. The design of the peptides in this example was based on the amino acid sequence of HR2 as well as its active state conformation. Successful viral entry occurs when HR2 and HR1 conformational changes during post fusion result in the formation of a six-helix bundle. Therefore, the HR2 peptides in this example (FIG. 1A-C) were designed to have a helical structure by the strategic insertion of cysteines pairs within the sequence. The cysteines used in this example were commonly separated by 7 amino acids to allow for the formation of disulfide bridges. This strategy to stabilize the tertiary conformation of the peptides was chosen due, in part to its resemblance to the wild type HR2 peptide. Moreover, this approach avoided the introduction of non-amino acid residues for stabilizing the peptides, as compared to other lengthy chemical methods used in the literature[8] for stabilizing a helical peptide.

A 3D modeling software was used to predict the position of the cysteines so that they will form disulfide bonds (FIG. 1B). When cysteine pairs were placed 7 residues apart at the beginning and the end of the sequence (from the N-terminal to C-terminal), the peptide was predicted to have a helical conformation. Thus, each pair of cysteines was inserted at the beginning and/or end of the sequence in order to stabilize the helix and increase protease resistance through disulfide bonding. The predictions made by the modeling software were later confirmed by CD of the purified peptides (FIG. 1C). It was interesting to observe a trend between the degree of helicity and the number of cysteines pairs in the peptide. In the case of HR2-S (one cysteine pair at the N-terminal), the trend is predominantly helical; however, the degree of rotation did not occur on the positive side of the axis. This could be due to interference by some random structure within the peptide conformation, or by the presence of traces of side products still existing after purification. With HR2-D (two cysteine pairs, N-terminal and C-terminal regions), the CD spectrum clearly shows a large degree of rotation from positive to negative values on the y-axis, which is a sign of helicity.[20,21] Moreover, when the peptide was too short to allow the insertion of two pairs of cysteines (HR2-B, HR2-C), the CD turned out showing a random structure (data not shown).

Progress of infection in the prophylactic method was followed using viral titers and flow cytometry on cells treated with two doses of peptide and infected with RSV (FIGS. 3A-3B). From flow cytometry experiments (FIG. 2), cells treated with HR2-D and HR2-S showed less GFP expression when infected with RG RSV, as compared to the untreated cell positive control. Of all the modified peptides tested HR2-D showed the greatest inhibition of RG RSV infection. On the other hand HR2-S was the most effective inhibitor when tested in cells infected with RA2 strain of RSV. Thus, to further characterize the effect of peptides HR2-D and HR2-S against RSV strains, viral titers were measured by plaque assay in HEp-2 cells infected with RSV strains A2 or rA2 and incubated with 5 μM peptide HR2-S (one disulfide) or HR2-D (two disulfides). Although there was a variation in the response to the same peptide treatment using the two different strains (RA2<GFP-RSVA2), HR2-D and HR2-S triggered the lowest infection for all the strains tested. The antibody used seemed not specifically binding to HR2 or HR1 epitopes, explaining the variability in the results.

In order to further investigate the activity of HR2-D and HR2-S, viral titers were measured at three different time points (24-96 h) after infection with two RSV strains (A2 and RA2), FIGS. 3A and B, respectively. HR2-S did not block A2 infection effectively, but did inhibit RA2 infection. HR2-D showed greater inhibitory activity especially with regard to the A2 strain. Thus, these results showed that HR2-D (2 cysteine pairs) and HR2-S (1 cysteine pair) were not following a unique pattern of infectivity in the different virus strains tested. This could be due to the response of the peptide itself or the limited specificity of the anti RSV antibody. Thus a set of peptides (HR2-D0-HR2-D4) were designed to confirm the predictions from the modeling software in regards to the formation of disulfide bonds (between amino acids 3 and 10, and/or 19 and 26) and their RSV antiviral activity (FIG. 4A, B). The lack of activity seen in HR2-D0 demonstrated that the activity of HR2-D is due to disulfide bonding and not simply to length or the helical structure. HR2-D contains 4 cysteines and thus can form two disulfides while HR2-D1 and HR2-D2 have only 3 cysteines and can have only one disulfide, either at the C-terminus (HR2-D1) or at the N-terminus (HR2-D2). Disulfide bonding between residues 9 and 16 in HR2-D1 seems to be critical. This is an indication that disulfide bridges between cys 9 and 32 or 16 and 25 are less likely to occur, as also predicted by the modeling software (FIG. 2A). The in vitro data shown here (FIG. 4B) for a series of HR2 peptides demonstrate that HR2-D is a good candidate for preventing RSV infection. In order to test HR2-D activity in vivo, however, the peptide must be administered at a low dose in order to decrease cytotoxicity and should have an extended half-life to allow continued activity.

Also, one of the major weakness of inhibitory peptides is their use either as prophylactic or therapeutic drugs. We reasoned that the plasma stability of peptides can be improved by using MPs, FMPs (FIGS. 5, 6, 7, 8) or FM-HR2-D (FIGS. 9, 10, 11) as their carriers.

Micelles filled with HR2-S and conjugated to HR2-D (FMP) are larger than micelles with empty cores (MP),[16] measuring 24 nm in size diameter (FIG. 6A). The narrow peak distribution for FMPs reveals the presence of a dominant size population in the sample, which can only be achieved if the micelle is tightly packed after peptide encapsulation in its core. However, due to the small size of the peptide, it is difficult to estimate from DLS how many layers of peptide are on the surface of the micelle. Successful internalization was visualized with confocal microscopy (FIG. 6B) and quantified using flow cytometry on Vero and Hep2 cells after treatment with Cy5 labeled MPs (FIG. 7B). Free peptides or labeled MPs were tested for their anti-RSV activity at low and high RG RSV concentrations (FIGS. 7A and 7B). Labeled MPs were used to quantify the uptake of micelles using a higher virus concentration. GFP expression was higher under these conditions for all the treatments, however the same trend was observed. MPs of HR2-D were the most efficient in reducing infection at low (95% reduction) and high (85% reduction) virus concentration. Notably, MPs alone (one of the controls) reduced infection by 50% at high and low RGRSV concentration. This could be just due to steric effects of the micelles which are found occasionally attached to the outer surface of the cell membrane (from confocal imaging), thereby physically blocking the interactions between virus fusion protein and its host. However, it is difficult to determine by flow cytometry if the MPs are inside or outside the cell membrane. The peptide release from the MPs was demonstrated by the good inhibitory results (85% neutralization), when compared with micelle control (40% neutralization) and peptide control levels (70% neutralization), respectively.

Figure 9:
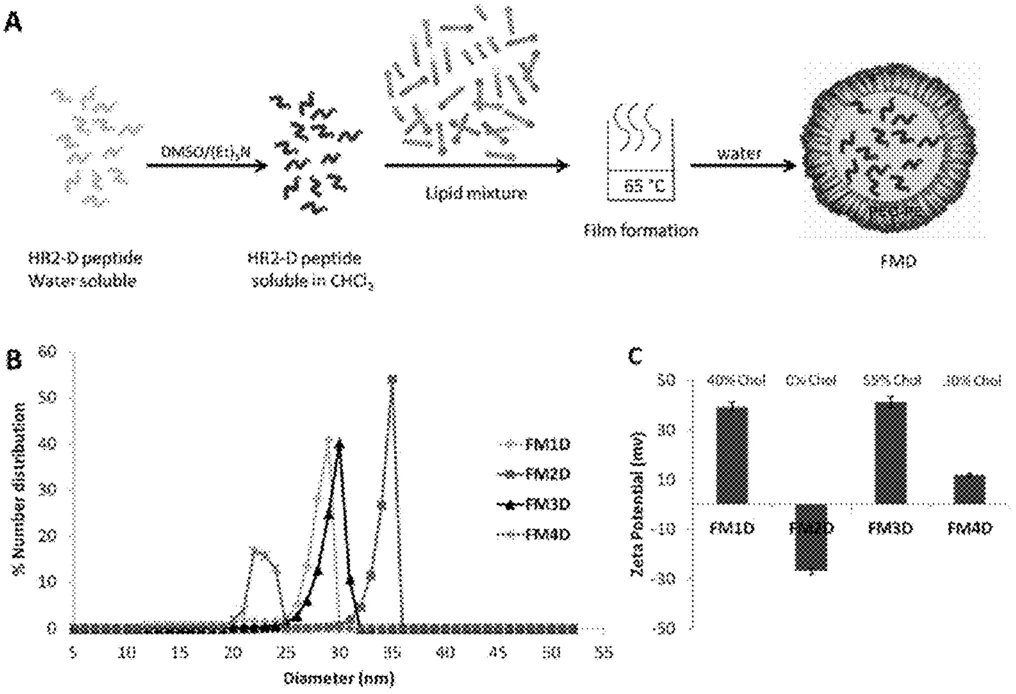
FIG. 9A is a schematic illustration of a self-assembly model of FMDs.
FIGS. 9B and 9C illustrate characterization by dynamic light scattering and zeta potential, respectively.

Epifluorescence microscopy and flow cytometry in A549 cells treated prophylactically (FIGS. 8A-8B) revealed the same pattern of inhibitory activity seen in RG RSV infected Vero cells. This result shows that this treatment can be successfully translated from monkey epithelial cells to human adenocarcinoma epithelial cells, despite the negatively charged environment existing at the cell membrane of a cancer cell. FMPs and MPs had similar response in the prophylactic model (90% inhibition, FIG. 8B). The same trend was observed when comparing MPs and FMPs in the therapeutic approach (50% inhibition, FIG. 8D). This indicated that in the case of FMP, HR2-S in the core has not been appreciably released after 24 h, presumably due to limited release of the peptide from its core or that the peptide used in the micelle core (HR2-S) lost antiviral activity when its hydrophobicity was modified. Therefore, the micelle composition was redesigned to make sure it would break shortly after administered to the infected cells and release its cargo. Therefore, the formulation of the micelles was altered, and HR2-D was as the unique cargo, a peptide that had proven inhibitory activity and stability in different cell lines. These next generations of micellar nanoparticles containing HR2-D in its core were termed as FMDs (FIG. 9).

The dynamic light scattering and zeta potential measurements on FMD micelles showed a clear trend between the size and the surface charge (FIGS. 9B and 9C). FM1 D and FM3D contain high amounts of DC-cholesterol (40 and 55% respectively), which imparts less fluidity to the micelles and thus favors compact assembly. The FM1 D and FM3D diameters are consistent with a micelle having a 20 nm core, as described previously in the literature.[24] Furthermore, the zeta potential values for FMD1 and FMD3 corroborated a highly positively charged surface on the micelles. It is to be noted that both FM1 D and FM3D have similar charge (FIG. 9C) on their surface although the amount of cholesterol was higher for FM3D (55%). This is an indication that 40% cholesterol content (FM1D) might be the threshold amount of positive charge that can be used to form a stable micelle in water due to electrostatic repulsion. The predominant lipid in the FM4D formulation was a small cationic lipid, DSPC. Due to its small size compared to the other lipids, DSPC defined the size of FM4D micelles. The core of these conjugates was smaller than FM1 D (20 nm core). Thus, FM4D would be able to encapsulate only about half fold of peptides than FM1 D or FM3D, in terms of their core sizes. Despite the fact that DSPC is a cationic lipid, the length of DSPC is smaller than the length of the other lipids involved in the FM4D formulation; thus, it seems it remains hindered and does not contribute to surface charge. In order to test this observation, another formulation (FM2D) was prepared with no cholesterol. It was expected that the hydrodynamic size of FM2D would be larger than the other three formulations. Due to the absence of cholesterol, the surface groups on the lipids were not facing electrostatic repulsions and thus a more fluidic micelle size (bigger size, bigger core) was observed with a strong negative zeta potential due to phosphate groups in the phospholipids (FIGS. 9B and 9C). Therefore, it was demonstrated that cholesterol accounts for surface charge.

From DLS and zeta potential analysis, FM2D and FM3D were chosen for testing their inhibitory effect, since FM2D is the most fluid (bigger core, more peptide encapsulated) and FM3D is more packed with a high positive surface charge. Moreover, a cellular uptake experiment was carried out using DOX instead of peptide as the cargo inside the FMDs (data not shown). From uptake experiments, it was observed that all FMDs release their cargo efficiently after 4 h post treatment. In particular, FM2D and FM3D showed best uptake efficiency up to 24 h post treatment in LLC1 (mouse derived Lewis Lung Cancer cells) cell line (data not shown). Based on uptake experiments, zeta potential and DLS results, FM2D and FM3D were selected for therapeutic experiments using RG RSV. The reduction in the GFP expression levels was followed by microscopy (FIG. 10B) and quantified using flow (FIG. 10C, D). Both FM2D and FM3D reduced GFP expression in infected cells to statistically significant values corresponding to $P<0.01$. Thus, FMDs were more efficient in reducing infectivity administered after 24 h of infection (with RG RSV at low MOI), and the reduction in the GFP expression levels was statistically more significant than in case of FMPs (FIG. 8D).

From the results illustrated in FIG. 11, it is evident that HR2-D peptide encapsulated inside micelles has long term activity as shown by confocal imaging after 6 h post infection. It is shown that the peptide inside the cells are colocalizing with the virus after micelles have attached to the cell surface and released the peptide inside the cells. In addition, it was observed that micelles colocalized with the virus in the vicinity of the cells. This is an indication that micelles also help in preventing virus entry by physically blocking virus ability to interact with the cell membrane. Furthermore, robust capping of micelles protects the peptides and guides them to the cell membrane. This was corroborated by green labeled peptide, purple labeled micelle and orange labeled virus outside the cells (FIG. 11E). While at the cell membrane, only purple and orange signals colocalized.

Figure 12:
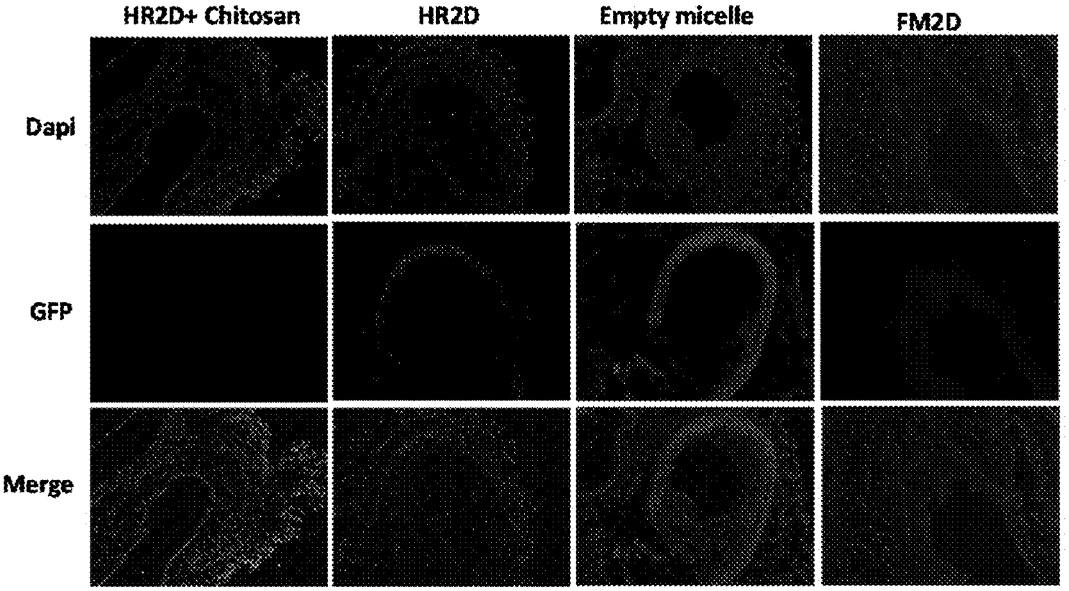
FIG. 12 is a series of images of nose sections illustrating that HR2D peptide is effective in vivo. Ten week old BALB/c mice (n=4 per group) were anesthetized and treated intranasally with the indicated HR2D peptide (125 μM in 1.2% DMSO) or packaged in filled micelles or with chitosan nanoparticles and empty micelles control. One hour post reatment, three groups of mice were inoculated with a single dose of rgRSV at $1\times10^6$ pfu/mouse. Mice were sacrificed at 24 hours post infection and the noses harvested, sectioned, stained with DAPI and imaged for GFP using an Olympus fluorescent microscope.

As RSV mainly infects through nasal route, and nasal RSV infection can spread to the lungs and cause bronchiolitis and pneumonia, this example also investigated if intranasal delivery of peptides or peptide nanocomplexes could prevent the development of pulmonary RSV infection. Treatment with HR2D alone significantly decreased virus infected cells in the nose after 24 h post infection. Further, treatment with micelles or chitosan nanoparticles containing HR2D completely abrogated any infected cells in the nose after 24 h post-infection (FIG. 12). Thus, this data demonstrated that pretreatment with HR2D peptide micelles or HR2D chitosan nanocomplexes can substantially decrease or prevent RSV infection in vivo.

CONCLUSIONS

The peptide HR2-D efficiently inhibited RSV infection in vitro, reducing the virus infectivity by 80% when administered prophylactically. The stability of the peptide was attributed to the formation of disulfide bonds, with the one cysteine at the N-terminus of HR2-D being crucial for the inhibitory activity of these series of peptides. MPs inhibited RSV infection at low and high MOI in Vero and A549. HR2-D-MPs had greater antiviral activity than free peptide in the prophylactic model of infection, but FMPs did not appear to be as effective inhibitors when administered therapeutically after infection. FMP reduced infectivity by 55% compared to positive control. The next generation of nanoformulations, FMDs, were successful in reducing the virus infectivity by 80% when administered under therapeutic conditions. Also, in an in vivo nasal RSV infection model, pretreatment with HR2D peptide micelles or HR2D chitosan nanocomplexes showed a substantial decrease or complete abrogation of RSV infected cells in the noseafter 24 h of infection.

FM2Ds were better at protecting the HR2-D cargo and releasing it over a longer period of time, conferring a long-lasting protection as compared to free peptide or FMPs. It seems that the negative charge on these nanomicelles helps them to neutralize more effectively the virus interaction with its host. The longer antiviral activity of FM2D could be explained in terms of the negative surface charge of the micelles being attractive to the positive residues on the virus surface. Thus, when the micelles break, the RSV F protein is readily available to bind to HR2-D. Another reason for the good inhibitory activity of FM2D could be the electrostatic repulsion between the cell membrane and the micelle surface, which might keep them in close proximity to the cells and blocking the interaction between the RSV F and its host.

References, each of which is incorporated by reference herein.

1. Lindell, D. M.; Morris, S. B.; White, M. P.; Kallal, L. E.; Lundy, P. K.; Hamouda, T.; Baker, J. R., Jr.; Lukacs, N. W., A Novel Inactivated Intranasal Respiratory Syncytial Virus Vaccine Promotes Viral Clearance without Th2 Associated Vaccine-Enhanced Disease. *PLoS ONE* 2011, 6 (7), e21823.
2. Roymans, D.; Koul, A., Treatment of Respiratory Syncytial Virus Infection: Past, Present and Future, Human Respiratory Syncytial Virus Infection, Bernhard Resch (Ed.) 2011, ISBN: 978-953-307-718-5.
3. Roymans, D.; Koul, A., Respiratory syncytial virus: a prioritized or neglected target? *Future Medicinal Chemistry* 2010, 2 (10), 1523-1527.
4. Hall, C. B., Respiratory Syncytial Virus and Parainfluenza Virus. *New England Journal of Medicine* 2001, 344 (25), 1917-1928.
5. Powell, K. L.; Alber, D., Development of Antivirals against Respiratory Syncytial Virus. In *Perspectives in Medical Virology*, Patricia, C., Ed. Elsevier: 2006; Vol. Volume 14, pp 279-298.
6. Openshaw, P. J. M.; Dean, G. S.; Culley, F. J., Links between respiratory syncytial virus bronchiolitis and childhood asthma: clinical and research approaches. *The Pediatric Infectious Disease Journal* 2003, 22 (2), S58-S65.

7. Ding, W.-d.; Mitsner, B.; Krishnamurthy, G.; Aulabaugh, A.; Hess, C. D.; Zaccardi, J.; Cutler, M.; Feld, B.; Gazumyan, A.; Raifeld, Y.; Nikitenko, A.; Lang, S. A.; Gluzman, Y.; O'Hara, B.; Ellestad, G. A., Novel and Specific Respiratory Syncytial Virus Inhibitors That Target Virus Fusion. *Journal of Medicinal Chemistry* 1998, 41 (15), 2671-2675.
8. Lambert, D. M.; Barney, S.; Lambert, A. L.; Guthrie, K.; Medinas, R.; Davis, D. E.; Bucy, T.; Erickson, J.; Merutka, G.; Petteway, S. R., Peptides from conserved regions of paramyxovirus fusion (F) proteins are potent inhibitors of viral fusion. *Proceedings of the National Academy of Sciences* 1996, 93 (5), 2186-2191.
9. Adams, O.; Bonzel, L.; Kovacevic, A.; Mayatepek, E.; Hoehn, T.; Vogel, M., Palivizumab-Resistant Human Respiratory Syncytial Virus Infection in Infancy. *Clinical Infectious Diseases* 2010, 51 (2), 185-188.
10. Zhao, X.; Chen, F.-P.; Sullender, W. M., Respiratory syncytial virus escape mutant derived in vitro resists palivizumab prophylaxis in cotton rats. *Virology* 2004, 318 (2), 608-612.
11. Zhao, X.; Chen, F.-P.; Megaw, A. G.; Sullender, W. M., Variable Resistance to Palivizumab in Cotton Rats by Respiratory Syncytial Virus Mutants. *Journal of Infectious Diseases* 2004, 190 (11), 1941-1946.
12. Bird, G. H.; Madani, N.; Perry, A. F.; Princiotto, A. M.; Supko, J. G.; He, X.; Gavathiotis, E.; Sodroski, J. G.; Walensky, L. D., Hydrocarbon double-stapling remedies the proteolytic instability of a lengthy peptide therapeutic. *Proceedings of the National Academy of Sciences* 2010, 107 (32), 14093-14098.
13. Roymans, D.; De Bondt, H. L.; Arnoult, E.; Geluykens, P.; Gevers, T.; Van Ginderen, M.; Verheyen, N.; Kim, H.; Willebrords, R.; Bonfanti, J.-F.; Bruinzeel, W.; Cummings, M. D.; van Vlijmen, H.; Andries, K., Binding of a potent small-molecule inhibitor of six-helix bundle formation requires interactions with both heptad-repeats of the RSV fusion protein. *Proceedings of the National Academy of Sciences* 2010, 107 (1), 308-313.
14. Cianci, C.; Langley, D. R.; Dischino, D. D.; Sun, Y.; Yu, K.-L.; Stanley, A.; Roach, J.; Li, Z.; Dalterio, R.; Colonno, R.; Meanwell, N. A.; Krystal, M., Targeting a binding pocket within the trimer-of-hairpins: Small-molecule inhibition of viral fusion. *Proceedings of the National Academy of Sciences of the United States of America* 2004, 101 (42), 15046-15051.
15. Gruber, H. J.; Kada, G.; Pragl, B.; Riener, C.; Hahn, C. D.; Harms, G. S.; Ahrer, W.; Dax, T. G.; Hohenthanner, K.; Knaus, H.-G., Preparation of Thiol-Reactive Cy5 Derivatives from Commercial Cy5 Succinimidyl Estert. *Bioconjugate Chemistry* 2000, 11 (2), 161-166.
16. Dubertret, B.; Skourides, P.; Norris, D. J.; Noireaux, V.; Brivanlou, A. H.; Libchaber, A., In Vivo Imaging of Quantum Dots Encapsulated in Phospholipid Micelles. *Science* 2002, 298 (5599), 1759-1762.
17. Ling, Z.; Tran, K. C.; Arnold, J. J.; Teng, M. N., Purification and characterization of recombinant human respiratory syncytial virus nonstructural protein NS1. *Protein Expression and Purification* 2008, 57 (2), 261-270.
18. Boyapalle, S.; Wong, T.; Garay, J.; Teng, M.; San Juan-Vergara, H.; Mohapatra, S.; Mohapatra, S., Respiratory Syncytial Virus NS1 Protein Colocalizes with Mitochondrial Antiviral Signaling Protein MAVS following Infection. *PLoS ONE* 2012, 7 (2), e29386.
19. San-Juan-Vergara, H.; Sampayo-Escobar, V.; Reyes, N.; Cha, B.; Pacheco-Lugo, L.; Wong, T.; Peeples, M. E.; Collins, P. L.; Castaño, M. E.; Mohapatra, S. S., Cholesterol-Rich Microdomains as Docking Platforms for Respiratory Syncytial Virus in Normal Human Bronchial Epithelial Cells. *Journal of Virology* 2012, 86 (3), 1832-1843.
20. Matthews, J. M.; Young, T. F.; Tucker, S. P.; Mackay, J. P., The Core of the Respiratory Syncytial Virus Fusion Protein Is a Trimeric Coiled Coil. *Journal of Virology* 2000, 74 (13), 5911-5920.
21. Wang, E.; Sun, X. o.; Qian, Y.; Zhao, L.; Tien, P.; Gao, G. F., Both heptad repeats of human respiratory syncytial virus fusion protein are potent inhibitors of viral fusion. *Biochemical and Biophysical Research Communications* 2003, 302 (3), 469-475.
22. Dixit, S. K.; Goicochea, N. L.; Daniel, M.-C.; Murali, A.; Bronstein, L.; De, M.; Stein, B.; Rotello, V. M.; Kao, C. C.; Dragnea, B., Quantum Dot Encapsulation in Viral Capsids. *Nano Letters* 2006, 6 (9), 1993-1999.
23. Trent, A.; Marullo, R.; Lin, B.; Black, M.; Tirrell, M., Structural properties of soluble peptide amphiphile micelles. *Soft Matter* 2011, 7 (20), 9572-9582.
24. Huang, X.; Bronstein, L. M.; Retrum, J.; Dufort, C.; Tsetkova, I.; Aniagyei, S.; Stein, B.; Stucky, G.; McKenna, B.; Remmes, N.; Baxter, D.; Kao, C. C. and Dragnea, B. Self-Assembled Virus-like Particles with Magnetic Cores. *Nano Letters* 2007, 7 (8), 2407-2416.

The invention claimed is:

1. An isolated polypeptide comprising an amino acid sequence selected from the group consisting of: SEQ ID NO:2, SEQ ID NO:4, SEQ ID NO:6, SEQ ID NO:7, and SEQ ID NO:10.

2. The isolated polypeptide of claim 1, wherein the amino acid sequence is SEQ ID NO:2.

3. The isolated polypeptide of claim 1, wherein the amino acid sequence is SEQ ID NO:7.

4. The isolated polypeptide of claim 1, wherein the isolated polypeptide consists essentially of: an amino acid sequence selected from the group consisting of SEQ ID NO:2, SEQ ID NO:4, SEQ ID NO:6, SEQ ID NO:7, and SEQ ID NO:10.

5. A composition comprising a micelle having a lipid layer and a core, wherein the core comprises a first polypeptide, and wherein the first polypeptide comprises an amino acid sequence selected from the group consisting of SEQ ID NO:2, SEQ ID NO:4, SEQ ID NO:6, SEQ ID NO:7, and SEQ ID NO:10.

6. The composition of claim 5, wherein the amino acid sequence is SEQ ID NO:7 or SEQ ID NO:2.

7. The composition of claim 5, wherein the first polypeptide consists essentially of an amino acid sequence selected from the group consisting of: SEQ ID NO:2, SEQ ID NO:4, SEQ ID NO:6, SEQ ID NO:7, and SEQ ID NO:10.

8. The composition of claim 5, wherein the lipid layer comprises amine-PEG-PE.

9. The composition of claim 5, wherein the lipid layer comprises amine-PEG-PE, methoxy-PEG-PE, and DSPC, and wherein the first polypeptide comprises SEQ ID NO:7.

10. The composition of claim 9, wherein the micelle is prepared with about 20% amine-PEG-PE, about 20% methoxy-PEG-PE, and about 60% DSPC.

11. The composition of claim 5, further comprising a coating, wherein the coating comprises a second polypeptide, wherein the second polypeptide comprises an amino acid sequence selected from the group consisting of SEQ ID NO:2, SEQ ID NO:4, SEQ ID NO:6, SEQ ID NO:7, and SEQ ID NO:10.

12. The composition of claim 11, wherein the first polypeptide comprises SEQ ID NO:2 and the second polypeptide comprises SEQ ID NO:7.

13. The composition of claim 11, wherein the first polypeptide consists essentially of SEQ ID NO:7 and the second polypeptide consists essentially of SEQ ID NO:2.

* * * * *

UNITED STATES PATENT AND TRADEMARK OFFICE

CERTIFICATE OF CORRECTION

PATENT NO. : 9,556,236 B1
APPLICATION NO. : 14/093107
DATED : January 31, 2017
INVENTOR(S) : Shyam S. Mohapatra et al.

It is certified that error appears in the above-identified patent and that said Letters Patent is hereby corrected as shown below:

In the Specification

Column 1 Lines 17-21: Change "This invention was made with Government support under NCI grant IROICA152005-01 and NIH grant P30HL101265-01. The Government has certain rights in this invention." to -- This invention was made with government support HL101265 and CA152005 awarded by the National Institutes of Health. The Government has certain rights in the invention. --

Signed and Sealed this
Thirtieth Day of January, 2018

Joseph Matal

*Performing the Functions and Duties of the*
*Under Secretary of Commerce for Intellectual Property and*
*Director of the United States Patent and Trademark Office*